United States Patent
Brown et al.

(10) Patent No.: US 9,833,768 B2
(45) Date of Patent: *Dec. 5, 2017

(54) AFFINITY REAGENTS FOR PROTEIN PURIFICATION

(71) Applicants: Impossible Foods Inc., Redwood City, CA (US); The Board of Trustees of the Leland Stanford Junior University, Stanford, CA (US)

(72) Inventors: Patrick O'Reilly Brown, Stanford, CA (US); R. Edward Watts, Palo Alto, CA (US); Pehr Harbury, Portola Valley, CA (US)

(73) Assignees: Impossible Foods Inc., Redwood City, CA (US); The Board of Trustees of the Leland Stanford Junior University, Stanford, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/661,754

(22) Filed: Jul. 27, 2017

(65) Prior Publication Data

US 2017/0320041 A1  Nov. 9, 2017

Related U.S. Application Data

(63) Continuation of application No. 14/385,586, filed as application No. PCT/US2013/032675 on Mar. 15, 2013, now Pat. No. 9,737,875.

(60) Provisional application No. 61/611,999, filed on Mar. 16, 2012.

(51) Int. Cl.
| | |
|---|---|
| *C07D 251/70* | (2006.01) |
| *C07D 401/04* | (2006.01) |
| *C07D 401/14* | (2006.01) |
| *C07D 403/04* | (2006.01) |
| *C07D 403/14* | (2006.01) |
| *C07D 413/04* | (2006.01) |
| *C07D 413/14* | (2006.01) |
| *A61K 31/53* | (2006.01) |
| *C07K 1/22* | (2006.01) |
| *B01J 20/281* | (2006.01) |
| *B01J 20/286* | (2006.01) |
| *B01J 20/32* | (2006.01) |
| *C07D 251/54* | (2006.01) |
| *G01N 33/68* | (2006.01) |
| *G01N 33/543* | (2006.01) |
| *G01N 33/28* | (2006.01) |

(52) U.S. Cl.
CPC ............ *B01J 20/281* (2013.01); *A61K 31/53* (2013.01); *B01J 20/286* (2013.01); *B01J 20/3204* (2013.01); *B01J 20/3212* (2013.01); *B01J 20/3248* (2013.01); *B01J 20/3251* (2013.01); *C07D 251/54* (2013.01); *C07D 251/70* (2013.01); *C07K 1/22* (2013.01); *G01N 33/543* (2013.01); *G01N 33/6818* (2013.01)

(58) Field of Classification Search
CPC .. C07D 251/70; C07D 401/04; C07D 401/14; C07D 403/04; C07D 403/14; C07D 413/04; C07D 413/14; A61K 31/53
USPC ............... 544/196, 197, 198; 514/245, 231.5
See application file for complete search history.

(56) References Cited

U.S. PATENT DOCUMENTS

| | | | |
|---|---|---|---|
| 5,582,988 A | 12/1996 | Backus et al. | |
| 7,479,472 B1 | 1/2009 | Harbury et al. | |
| 9,737,875 B2 * | 8/2017 | Brown et al. ........ | C07D 251/70 544/198 |
| 2003/0166002 A1 | 9/2003 | Chang et al. | |
| 2008/0261202 A1 | 10/2008 | Baker et al. | |
| 2009/0004641 A1 | 1/2009 | Gee et al. | |
| 2010/0173889 A1 | 7/2010 | Schunk et al. | |
| 2015/0087532 A1 * | 3/2015 | Brown ..................... | C07K 1/22 506/3 |

FOREIGN PATENT DOCUMENTS

| | | |
|---|---|---|
| WO | WO 2001/047921 | 7/2001 |
| WO | WO 2005/049653 | 6/2005 |
| WO | WO 2011/012302 | 2/2011 |
| WO | WO 2013/138793 | 9/2013 |

OTHER PUBLICATIONS

Supplementary Methods for Clark et al. "Design Synthesis and Selection of DNA-Encoded Small Molecule Libraries," Nature Chemical Biology, doi:10.1038/nchembio.211, 57 pages (Sep. 2009).
Albercio and Carpino, "Coupling reagents and activation," Methods in Enzymology, 289:104-126 (1997).
Chen et al., "One bead-one compound combinatorial peptide library: different types of screening," Methods in Enzymology, 267:211-219 (1996).
Clark et al., "Design, synthesis and selection of DNA-encoded small-molecule libraries," Nature Chemical Biology, , 5(9): 647-654 (Sep. 2009).
Das et al., "Biofunctionalized pH-Responsive Microgels for Cancer Cell Targeting: Rational Design," Adv. Mater, 2006, 18:80-83.
Deng et al., "Hollow chitosan-silica nanospheres as pH-sensitive targeted delivery carriers in breast cancer therapy," Biomaterials, Mar. 2011, 32(21):4976-4986.
Ellman and Gallop, "Combinatorial Chemistry," Curr Opin Chem Biol, 2:317-319 (1998).
European Communication pursuant to Rule 164(1) EPC in European Application No. 13760954.1, dated Dec. 4, 2015, 8 pages.
Fisher et al., "Metal ion chelating peptoids with potential as anti-oxidants: complexation studies with cupric ions," J. Inorganic Biochemistry, Dec. 2003, 98(2): 343-346.
Hianik et al., "Influence of ionic strength, pH and aptamer configuration for binding affinity to thrombin," Bioelectrochemistry, Dec. 2006, 70(1):127-133.

(Continued)

*Primary Examiner* — Venkataraman Balasubramanian
(74) *Attorney, Agent, or Firm* — Fish & Richardson P.C.

(57) ABSTRACT

Disclosed herein are methods and compositions for purifying proteins from crude solutions.

9 Claims, No Drawings

(56) References Cited

OTHER PUBLICATIONS

International Preliminary Report on Patentability in International Application No. PCT/US2013/032675, dated Nov. 13, 2014, 9 pages.
International Search Report and Written Opinion in International Application No. PCT/US/13/32675, dated Aug. 5, 2013, 18 pages.
International Search Report and Written Opinion in International Application No. PCT/US14/56568, dated Dec. 12, 2014.
Knockaert et al., "Intracellular targets of cyclin-dependent kinase inhibitors: identification by affinity chromatography using immobilized inhibitors," Chemistry & Biology, 2000, 7:411-422.
Krishnamurty et al., "Protein kinase affinity reagents based on a 5-aminoindazole scaffold," Bioorg Med Chem Lett, 2011, 21(1):550-554.
Kudirka et al., "Folding of a single-chain, information-rich polypeptoid sequence into a highly ordered nanosheet," Biopolymers, Feb. 2011, 96(5):586-595.
Ranjitkar et al., "Affinity Reagents that Target a Specific Interactive form of Protein Kinases," Chem. Biol., 2010, 17(2):195-206.
Southern et al., "Arrays of complementary oligonucleotides for analysing the hybridisation behaviour of nucleic acids," Nucl. Acids Res., 22(8):1368-1373 (1994).
Vanhauteghem et al., "Glycine and its-methylated analogues cause pH-dependent membrane damage to enterotoxigenic," Amino Acids; The Forum for Amino Acid and Protein Research, Springer-Verlag, Sep. 2011, 43(1):245-253.
Wei et al., "Interaction of a novel peptoid enhancer—arginine oligomer with bovine submaxillary mucin," Yaoxue Xuebao, Dec. 2004, 39(12):1011-1017.
Wrenn et al., "Synthetic Ligands Discovered by In Vitro Selection," J Am Chem Soc, 129(43):13137-13143 (Oct. 2007).

\* cited by examiner

AFFINITY REAGENTS FOR PROTEIN PURIFICATION

CROSS-REFERENCE

This application is a continuation of U.S. application Ser. No. 14/385,586, filed Sep. 16, 2014, now U.S. Pat. No. 9,737,875, which is a National Stage application under 35 U.S.C. §371 of International Application No. PCT/US2013/032675 having an International Filing Date of Mar. 15, 2013, which claims the benefit of U.S. Provisional Application No. 61/611,999 filed Mar. 16, 2012, which applications are incorporated herein by reference.

BACKGROUND OF THE INVENTION

Proteins and other molecules with potential commercial value—for use as food ingredients (e.g., rubisco, seed-storage proteins, leghemoglobin), industrial enzymes (e.g., papain, bromelain, etc.), structural materials or pharmaceuticals are present in commercially useful quantities in natural sources. Purity of the protein or other molecule can be important for optimal utility.

The rarity of commercial sources of pure plant, animal or microbial proteins highlights an existing need in the art for general, scalable methods of efficiently and economically purifying proteins or other molecules from a crude solution.

SUMMARY OF THE INVENTION

Disclosed herein are methods for isolating one or more target proteins comprising: (a) applying a composition comprising the one or more target proteins to a substrate comprising one or more switchable affinity reagents at a binding pH such that the target proteins bind to the switchable affinity reagents; and (b) applying a solution at a release pH to the substrate comprising the one or more switchable affinity reagents such that the one or more target proteins are released from the one or more switchable affinity reagents, thereby isolating the one or more target proteins. Some embodiments further comprise (c) applying a wash solution at the binding pH between step (a) and step (b), wherein the wash solution removes one or more contaminants. In one embodiment, the one or more switchable affinity reagents do not comprise an antibody. In one embodiment, the one or more target proteins are antibodies. In one embodiment, the one or more target proteins can be used to treat a disease or disorder. In one embodiment, the disease or disorder is a cancer.

In some embodiments, the one or more target proteins comprise plant proteins. In one embodiment, said one or more target proteins are selected from the group consisting of leghemoglobin, non-symbiotic hemoglobin, hemoglobin, myoglobin, chlorocruorin, erythrocruorin, neuroglobin, cytoglobin, protoglobin, truncated 2/2 globin, HbN, cyanoglobin, HbO, Glb3, and cytochromes, Hell's gate globin I, bacterial hemoglobins, ciliate myoglobins, flavohemoglobins, ribosomal proteins, actin, hexokinase, lactate dehydrogenase, fructose bisphosphate aldolase, phosphofructokinases, triose phosphate isomerases, phosphoglycerate kinases, phosphoglycerate mutases, enolases, pyruvate kinases, proteases, lipases, amylases, glycoproteins, lectins, mucins, glyceraldehyde-3-phosphate dehydrogenases, pyruvate decarboxylases, actins, translation elongation factors, histones, ribulose-1,5-bisphosphate carboxylase oxygenase (rubisco), ribulose-1,5-bisphosphate carboxylase oxygenase activase (rubisco activase), albumins, glycinins, conglycinins, globulins, vicilins, conalbumin, gliadin, glutelin, gluten, glutenin, hordein, prolamin, phaseolin (protein), proteinoplast, secalin, extensins, triticeae gluten, collagens, zein, kafirin, avenin, dehydrins, hydrophilins, late embyogenesis abundant proteins, natively unfolded proteins, any seed storage protein, oleosins, caloleosins, steroleosins or other oil body proteins, vegetative storage protein A, vegetative storage protein B, moong seed storage 8S globulin, pea globulins, pea albumins, or combinations thereof.

In some embodiments, the one or more switchable affinity reagents comprise a small molecule compound. In some embodiments, the small molecule compound comprises peptide, peptoid, 3-peptide, or D-peptide subunits. In some embodiments, the binding pH is between about 7 and about 11. In some embodiments, the binding pH is about 9. In some embodiments, the release pH is between about 3 and about 7. In some embodiments, the release pH is about 6. In some embodiments, the one or more target proteins are used to produce a consumable. In some embodiments, the consumable is a meat-substitute. In some embodiments, the consumable is a cheese-substitute. In some embodiments, the consumable is a milk-substitute. In some embodiments, the consumable is an egg-substitute.

In some embodiments, the invention provides a composition comprising a non-polypeptide pH switchable reagent which binds a target at a first pH and does not bind the target at a second pH.

In some embodiments, the pH switchable reagent is a peptoid. In some embodiments, the peptoid is comprised of N subunits. In some embodiments, the N subunits are 1, 2, 3, 4, or 5 subunits. In some embodiments, N subunits is 2 subunits. In some embodiments, the peptoid is modified with multiple diversity points. In some embodiments, the multiple diversity points are at least 1, 2, 3, 4, 5, 6 diversity points. In some embodiments, the multiple diversity points are 4 diversity points.

In some embodiments, the peptoid comprises a triazine. In some embodiments, the triazine is tri-substituted.

In some embodiments, wherein the pH switchable reagent has a backbone structure comprising:

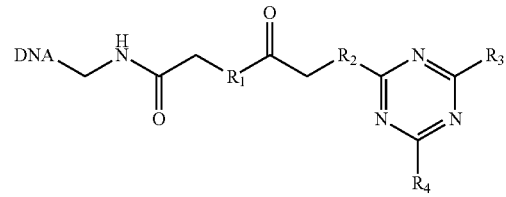

In some embodiments, the composition comprises a mixture of diastereomers. The composition can comprise a mixture of enantiomers. The composition can comprise an essentially pure diastereomer, wherein the essentially pure diastereomer refers to a diastereomer that is greater than 70% purified from other diastereomers. The composition can comprise an essentially pure enantiomer, wherein the essentially pure enantiomer refers to a enantiomer that is greater than 70% purified from other enantiomers.

In some embodiments, the peptoid is non-degradable by proteases.

In some embodiments, the first pH is greater than 7. In some embodiments, the first pH is less than 7. In some embodiments, the second pH is greater than 7. In some embodiments, the second pH is less than 7.

In some embodiments, the pH switchable reagent is conjugated to a substrate. In some embodiments, the substrate is a bead that is selected from a group comprising agarose, sepharose, polystyrene, styrene, iron oxide, magnetic, or paramagnetic. In some embodiments, the substrate is coated with a coat selected from a group comprising silica, carboxyl functional groups, aldehyde functional groups, or N-hydroxysuccinimide functional groups. In some embodiments, the substrate is coated with a functional group able to conjugate primary amines and thiols. In some embodiments, the substrate is a component of a resin used for chromatography. In some embodiments, the resin is used for protein purification chromatography. In some embodiments, the resin is used for affinity protein purification chromatography.

In some embodiments, the invention is a consumable product comprising a pH switchable reagent. In some embodiments, switchable reagent is present at a concentration of less than 1,000 parts per million target protein. In some embodiments, at least 90% of the dry weight of the composition comprises plant based protein. In some embodiments, the consumable is substantially free of chlorophylls, chlorins, metalloids, transition metals, celluloses, or complex polysaccharides. In some embodiments, the consumable product is food-safe.

In some embodiments, the composition comprises a protein content, wherein the protein content is obtained from a plant; wherein the composition is substantially free of odorants found in the plant. In some embodiments, the composition comprises the pH switchable reagent is present at a concentration of less than 1,000 parts per million target protein. In some embodiments, least 90% of the composition comprises plant based protein. In some embodiments, the composition is substantially free of chlorophylls, chlorins, metalloids, transition metals, celluloses, or complex polysaccharides. In some embodiments, the consumable product is food-safe.

In some embodiments, the composition comprises a protein content, wherein the protein content is obtained from a plant; wherein the composition is substantially free of colorants found in the plant. In some embodiments, the composition comprises the pH switchable reagent is present at a concentration of less than 1,000 parts per million target protein. In some embodiments, at least 90% of the composition comprises plant based protein. In some embodiments, the composition is substantially free of chlorophylls, chlorins, metalloids, transition metals, celluloses, or complex polysaccharides. In some embodiments, the consumable product is food-safe.

In some embodiments, the invention provides a method for identifying a non-polypeptide pH switchable reagent, the method comprising: a) generating a library of non-polypeptides by tag-directed synthesis; b) exposing at least a subset of the library to a protein in a solution at a first pH; c) altering the pH of the solution to a second pH; and d) identifying a non-polypeptide pH switchable reagent which binds a target at a first pH and does not bind the target at a second pH.

In some embodiments, the invention provides a method for isolating one or more target proteins comprising: a) applying a composition comprising the one or more target proteins to a substrate; wherein the substrate comprises one or more non-polypeptide pH switchable reagents; wherein at least part of the applying step occurs at a first pH; wherein at the first pH at least one of the one or more target proteins binds to the one or more non-polypeptide pH switchable reagents; b) releasing the target proteins by adjusting the pH of the solution to a second pH; wherein at the second pH at least one or more of the target proteins does not bind the non-polypeptide pH switchable reagent and; c) collecting the target proteins that eluted from the one or more non-polypeptide pH switchable reagents.

In some embodiments of the method, the pH switchable reagent is a peptoid. In some embodiments of the method, the peptoid is comprised of N subunits. In some embodiments of the method, N subunits is 1, 2, 3, 4, 5 subunits. In some embodiments of the method, N subunits is 2 subunits. In some embodiments of the method, the peptoid is modified with multiple diversity points. In some embodiments of the method, the multiple diversity points are at least 1, 2, 3, 4, 5, 6 diversity points. In some embodiments of the method, the multiple diversity points are 4 diversity points. In some embodiments of the method, the peptoid comprises a triazine. In some embodiments of the method, the triazine is tri-substituted. In some embodiments of the method, the pH switchable reagent has a backbone structure comprising:

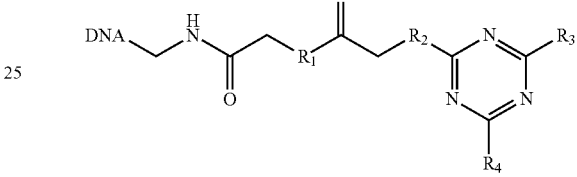

In some embodiments of the method, the pH switchable reagent comprises a mixture of diastereomers. In some embodiments of the method, the pH switchable reagent comprises a mixture of enantiomers. In some embodiments of the method, wherein the pH switchable reagent comprises an essentially pure diastereomer, wherein the essentially pure diastereomer refers to a diastereomer that is greater than 70% purified from other diastereomers. In some embodiments of the method, the pH switchable reagent comprises an essentially pure enantiomer, wherein the essentially pure enantiomer refers to an enantiomer that is greater than 70% purified from other enantiomers.

In some embodiments of the method, the peptoid is non-degradable by proteases. In some embodiments of the method, the first pH is greater than 7. In some embodiments of the method, the first pH is less than 7. In some embodiments of the method, the second pH is greater than 7. In some embodiments of the method, the second pH is less than 7.

In some embodiments of the method, the pH switchable reagent is conjugated to a substrate. In some embodiments of the method, the substrate is a bead that is selected from a group comprising agarose, sepharose, polystyrene, styrene, iron oxide, magnetic, or paramagnetic. In some embodiments of the method, the substrate is coated with a coat selected from a group comprising silica, carboxyl functional groups, aldehyde functional groups, amine functional groups, alkyne functional groups, azide functional groups or N-hydroxysuccinimide functional groups. In some embodiments of the method, the substrate is coated with a functional group able to conjugate primary amines and thiols. In some embodiments of the method, the substrate is a component of a resin used for chromatography. In some embodiments of the method, the resin is used for protein purification chromatography. In some embodiments of the method, the resin is used for affinity protein purification chromatography.

In some embodiments rubsco binds at pH 9 and releases at pH 6. In some embodiments rubsco binds at pH 6 and releases at pH 9. In some embodiments leghemoglobin binds at pH 9 and releases at pH 6. In some embodiments leghemoglobin binds at pH 6 and releases at pH 9.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Disclosed herein are methods and compositions for purifying one or more target proteins or compounds, or molecules from a crude solution. The methods and compositions disclosed herein can be used to purify quantities of the target proteins without the need to produce recombinant, tagged versions of the proteins. The methods and compositions can comprise switchable affinity reagents. The switchable affinity reagent can be a molecule that has controllable or regulatable affinity for a target protein, compound, or molecule. For example, a switchable affinity reagent can be a reagent that binds to the target protein, compound, or molecule with one affinity under a first set of conditions and does not bind, or binds with a lower affinity to, the target protein, compound, or molecule under a second set of conditions. The switchable affinity reagent can be a small molecule. The switchable affinity reagent can be designed. The switchable affinity reagent can be selected from a library of candidate affinity reagents or small molecules. The switchable affinity reagent can be selected from a library of candidate affinity reagents produced using DNA programmable combinatorial chemistry. The library of candidate affinity reagents, optionally produced using DNA programmable combinatorial chemistry, can be biased towards molecules that are likely to have a functional group or moiety that can be altered by environmental conditions. The switchable affinity reagent can be immobilized on a solid support structure, such as a bead or resin. The conditions to control or regulate the affinity of the switchable affinity reagent can include changes in pH, temperature, salinity, or concentration of a metal ion or other reagent.

Definitions

As used herein, "about" can refer to ±10% and includes ±1% and ±0.1%.

As used herein, in addition to definitions known in the art, "resin" can refer to a solid support with a large surface area (e.g. a membrane, a fine powder or gel.)

As used herein, the term "switchable affinity reagent" can mean a reagent that binds to a target (e.g. a protein) under one set of conditions but does not bind, or binds with a lower affinity to, the target under a second set of conditions.

Switchable Affinity Reagent

Methods to purify one or more targets (e.g., proteins from e.g. a crude solution) can utilize a switchable affinity reagent. The switchable reagent can be immobilized on a solid or semi-solid support. Conditions that can be used to regulate the affinity of a switchable affinity reagent for a target protein can include pH, temperature, salinity or ionic strength, or the concentration a metal ion or other reagent. In one example, the affinity of a switchable affinity reagent can be controlled by relying on pH dependent changes in charge of residues or chemical moieties on the target, the switchable affinity reagent, or both. The effected residues or chemical moieties can be located at the interface between the affinity reagent and the target. The effected residues or chemical moieties can be residues or chemical moieties whose charge affects the conformation of the affinity reagent, the target, or both. The switchable affinity reagent can comprise a small molecule compound. The switchable affinity reagent can optionally comprise a nucleic acid sequence that encodes a program for the synthesis of the small molecule compound. The switchable affinity reagent can be conjugated to a solid support substrate such as a bead. The switchable affinity reagent can be conjugated to a semi-solid support substrate.

A switchable affinity reagent can comprise a molecule or small molecule compound that is synthesized from smaller subunits, building blocks, or reagents, precursors, monomers or residues (collectively "subunits"). The subunits of a switchable affinity reagent can optionally comprise a common parent structure. The common parent structure can be a peptide or peptidomimetic backbone (e.g., an L-peptide backbone, a D-peptide backbone, a (3-peptide backbone, a peptoid backbone). The common parent structure can be a ring structure (e.g., a benzene ring, a phenol ring, a toluene, a napthalene, a cyclohexyl, a sugar, an aniline, a biphenyl structure, a pyridine, a triazine, etc.).

The common parent structure can comprise one or more (e.g., two) functional moieties that can be used to link subunits together. The subunits of the switchable affinity reagent can comprise, but are not limited to, L-amino acids or L-peptide residues, D-amino acids or D-peptide residues, (3-amino acids or 3-peptide residues, or peptoid residues).

The subunits can be comprised of one or more side chains or ring-structure modifications (collectively called "R groups") each of which can take a variety of chemical forms. The R groups of the subunits can vary in terms of chain length, ring size or number, and/or patterns of substitution. The R groups of the subunit of a switchable affinity reagent can comprise naturally occurring side chains such as the side chains found in L-peptides, proteins, or amino acids. The R groups of the subunits of a switchable affinity reagent can comprise side chains or groups not found in biology.

A switchable affinity reagent can comprise a molecule or small molecule compound that is synthesized from smaller subunits, building blocks, reagents, precursors, monomers, or residues (collectively "subunits"). The switchable affinity reagent can comprise between about 2 and about 1000 subunits; for example, the switchable affinity reagent can comprise about 2-1000, 2-750, 2-500, 2-250, 2-100, 2-75, 2-50, 2-40, 2-30, 2-25, 2-20, 2-15, 2-10, 2-5, 5-1000, 5-750, 5-500, 5-250, 5-100, 5-75, 5-50, 5-40, 5-30, 5-25, 5-20, 5-15, 5-10, 10-1000, 10-750, 10-500, 10-250, 10-100, 10-75, 10-50, 10-40, 10-30, 10-25, 10-20, 10-15, 15-1000, 15-750, 15-500, 15-250, 15-100, 15-75, 15-50, 15-40, 15-30, 15-25, 15-20, 20-1000, 20-750, 20-500, 20-250, 20-100, 20-75, 20-50, 20-40, 20-30, 30-1000, 30-750, 30-500, 30-250, 30-100, 30-75, 30-50, 30-40, 40-1000, 40-750, 40-500, 40-250, 40-100, 40-75, 40-50, 50-1000, 50-750, 50-500, 50-250, 50-100, 50-75, 75-1000, 75-750, 75-500, 75-250, 75-100, 100-1000, 100-750, 100-500, 100-250, 250-1000, 250-750, 250-500, 500-1000, 500-750, 750-1000, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 150, 200, 250, 300, 350, 400, 450, 500, 550, 600, 650, 700, 750, 800, 850, 900, 950, 1000. In one example, a switchable affinity reagent comprises between about 2 and about 10 subunits. In another example, the switchable affinity reagent comprises between about 2 and about 6 subunits. The switchable affinity reagent can optionally further comprise a nucleotide sequence (e.g., DNA, RNA) that encodes a program for the synthesis of the small molecule compound.

A switchable affinity reagent can be characterized by having a molecular weight of between about 10 Da and 1000000 Da; for example, the molecular weight of the switchable affinity reagent can be about 10-1000000 Da, 10-75000 Da, 10-50000 Da, 10-25000 Da, 10-10000 Da, 10-5000 Da, 10-2500 Da, 10-1000 Da, 10-750 Da, 10-500 Da, 10-250 Da, 10-100 Da, 100-1000000 Da, 100-75000 Da, 100-50000 Da, 100-25000 Da, 100-10000 Da, 100-5000 Da, 100-2500 Da, 100-1000 Da, 100-750 Da, 100-500 Da, 100-250 Da, 250-1000000 Da, 250-75000 Da, 250-50000 Da, 250-25000 Da, 250-10000 Da, 250-5000 Da, 250-2500 Da, 250-1000 Da, 250-750 Da, 250-500 Da, 500-1000000 Da, 500-75000 Da, 500-50000 Da, 500-25000 Da, 500-10000 Da, 500-5000 Da, 500-2500 Da, 500-1000 Da, 500-750 Da, 750-1000000 Da, 750-75000 Da, 750-50000 Da, 750-25000 Da, 750-10000 Da, 750-5000 Da, 750-2500 Da, 750-1000 Da, 1000-1000000 Da, 1000-75000 Da, 1000-50000 Da, 1000-25000 Da, 1000-10000 Da, 1000-5000 Da, 1000-2500 Da, 2500-1000000 Da, 2500-75000 Da, 2500-50000 Da, 2500-25000 Da, 2500-10000 Da, 2500-5000 Da, 5000-1000000 Da, 5000-75000 Da, 5000-50000 Da, 5000-25000 Da, 5000-10000 Da, 10000-1000000 Da, 10000-75000 Da, 10000-50000 Da, 10000-25000 Da, 25000-1000000 Da, 25000-75000 Da, 25000-50000 Da, 50000-1000000 Da, 50000-75000 Da, 75000-1000000 Da, 10 Da, 20 Da, 30 Da, 40 Da, 50 Da, 60 Da, 70 Da, 80 Da, 90 Da, 100 Da, 125 Da, 150 Da, 175 Da, 200 Da, 225 Da, 250 Da, 300 Da, 350 Da, 400 Da, 450 Da, 500 Da, 550 Da, 600 Da, 650 Da, 700 Da, 750 Da, 800 Da, 850 Da, 900 Da, 950 Da, 1000 Da, 1100 Da, 1200 Da, 1300 Da, 1400 Da, 1500 Da, 1600 Da, 1700 Da, 1800 Da, 1900 Da, 2000 Da, 2100 Da, 2200 Da, 2300 Da, 2400 Da, 2500 Da, 2750 Da, 3000 Da, 3250 Da, 3500 Da, 3750 Da, 4000 Da, 4250 Da, 4500 Da, 4750 Da, 5000 Da, 6000 Da, 7000 Da, 8000 Da, 9000 Da, 10000 Da, 12500 Da, 15000 Da, 17500 Da, 20000 Da, 22500 Da, 25000 Da, 30000 Da, 35000 Da, 40000 Da, 45000 Da, 50000 Da, 55000 Da, 60000 Da, 65000 Da, 70000 Da, 75000 Da, 80000 Da, 85000 Da, 90000 Da, 95000 Da, or 100000 Da, or more, or any intervening amount. In one example, the molecular weight of a switchable affinity reagent can be between about 100 Da and 1000 Da. In another example, the molecular weight of a switchable affinity reagent can be less than about 1000 Da.

In another example, the molecular weight of a switchable affinity reagent can be between about 600 and about 900 Da.

A switchable affinity reagent can be characterized as having a first binding affinity for a target protein, compound, or molecule under a first set of conditions (e.g., binding conditions) and a second binding affinity for the target protein under a second set of conditions (e.g., release conditions). The first binding affinity can be stronger than the second binding affinity. For example, the first binding affinity can be at least about 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, 1000, 1100, 1200, 1300, 1400, 1500, 1600, 1700, 1800, 1900, 2000, 2200, 2400, 2600, 2800, 3000, 3200, 3400, 3600, 3800, 4000, 4200, 4400, 4600, 4800, 5000, 5500, 6000, 6500, 7000, 7500, 8000, 8500, 9000, 9500, or 10000 times stronger than the second binding affinity.

A switchable affinity reagent can be characterized as having a first binding affinity for a target protein, compound, or molecule under a first set of conditions (e.g., binding conditions) and a second binding affinity for the target protein under a second set of conditions (e.g., release conditions), wherein the first binding affinity and the second binding affinity are expressed as dissociation constants ($K_d$). The dissociation constant can have molar units and a lower dissociation constant can mean that the switchable affinity reagent and the target protein bind with a higher affinity. Similarly, a higher dissociation constant can be associated with lower binding affinity between the switchable affinity reagent and the target protein. The first binding affinity between the switchable affinity reagent and the target protein can be a $K_d$ of less than about 2 mM; for example, the first binding affinity can be a $K_d$ of less than about 2 mM, 1000 uM, 900 uM, 800 uM, 700 uM, 600 uM, 500 uM, 400 uM, 300 uM, 200 uM, 100 uM, 75 uM, 50 uM, 25 uM, 20 uM, 15 uM, 10 uM, 9 uM, 8 uM, 7 uM, 6 uM, 5 uM, 4 uM, 3 uM, 2 uM, 1 uM, 900 nM, 800 nM, 700 nM, 600 nM, 500 nM, 400 nM, 300 nM, 200 nM, 100 nM, 75 nM, 50 nM, 25 nM, 20 nM, 15 nM, 10 nM, 9 nM, 8 nM, 7 nM, 6 nM, 5 nM, 4 nM, 3 nM, 2 nM, 1 nM, or lower. The second binding affinity can be a Kd that is at least about 2 times higher than the first binding affinity; for example, the second binding affinity can be a Kd that is at least about 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, 1000, 1100, 1200, 1300, 1400, 1500, 1600, 1700, 1800, 1900, 2000, 2200, 2400, 2600, 2800, 3000, 3200, 3400, 3600, 3800, 4000, 4200, 4400, 4600, 4800, 5000, 5500, 6000, 6500, 7000, 7500, 8000, 8500, 9000, 9500, or 10000 times higher than the first binding affinity.

pH Sensitive Switchable Affinity Reagents

A switchable affinity reagent can be a pH sensitive switchable reagent, wherein the reagent binds a target protein at a binding pH and does not bind the target protein at a release pH. The binding pH can be a pH between about 1 and 14; for example, about, 1, 2, 3, 4, 5, 6, 7, 8, 9, 10, 11, 12, 13, 14, or any included decimal. The release pH can be a pH between about 1 and 14; for example, about, 1, 2, 3, 4, 5, 6, 7, 8, 9, 10, 11, 12, 13, 14, or any included decimal. The binding and release pH can be separated by between about 1 and about 13 pH units; for example, the binding and release pH can be separated by about 1, 2, 3, 4, 5, 6, 7, 8, 9, 10, 11, 12, or 13 pH units. In some instances binding of a target protein occurs in acidic conditions and release of the target protein occurs in basic conditions. In some instances binding of a target protein occurs in basic conditions and release of the target protein occurs in acidic conditions. In one example, the binding pH can be between about 5 and 11 (e.g., about 5, 5.5, 6, 6.5, 7, 7.5, 8, 8.5, 9, 9.5, 10, 10.5, 11, or any included decimal) and the release pH can be between about 6 and about 11 (e.g., 6, 6.5, 7, 7.5, 8, 8.5, 9, 9.5, 10, 10.5, 11 or any included decimal). In another example, the binding pH can be between about 4 and about 8 (e.g., about 4, 4.5, 5, 5.5, 6, 6.5, 7, 7.5, 8 or any included decimal) and the release pH can be between about 7 and about 11 (e.g., 7, 7.5, 8, 8.5, 9, 9.5, 10, 10.5, 11, or any included decimal). In another example, the binding pH is about 6 and the release pH is about 9. In another example, the binding pH is about 9 and the release pH is about 6.

A pH sensitive switchable affinity reagent can be characterized by having a pKa of between about 1 and 14; for example, a pKa of about 1-14, 1-13, 1-12, 1-11, 1-10, 1-9, 1-8, 1-7, 1-6, 1-5, 1-4, 1-3, 1-2, 2-14, 2-13, 2-12, 2-11, 2-10, 2-9, 2-8, 2-7, 2-6, 2-5, 2-4, 2-3, 3-14, 3-13, 3-12, 3-11, 3-10, 3-9, 3-8, 3-7, 3-6, 3-5, 3-4, 4-14, 4-13, 4-12, 4-11, 4-10, 4-9, 4-8, 4-7, 4-6, 4-5, 5-14, 5-13, 5-12, 5-11, 5-10, 5-9, 5-8, 5-7, 5-6, 6-14, 6-13, 6-12, 6-11, 6-10, 6-9, 6-8, 6-7, 7-14, 7-13, 7-12, 7-11, 7-10, 7-9, 7-8, 8-14, 8-13, 8-12, 8-11, 8-10, 8-9, 9-14, 9-13, 9-12, 9-11, 9-10, 10-14, 10-13, 10-12, 10-11, 11-14, 11-13, 11-12, 12-14, 12-13, 13-14, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13, 13.1, 13.2, 13.3, 13.4, 13.5, 13.6, 13.7, 13.8, 13.9, 14. In one example, the pH sensitive switchable affinity reagent has a pKa of about 7 and is neutrally charged at a pH of about 9 and positively charged at a pH of about 5.

A Peptoid Switchable Reagent

In some instances the subunit is comprised of a peptoid backbone. The peptoid backbone is comprised of N peptoid subunits (sometimes referred to as oligo-N-substituted glycines), where the peptoid backbone subunit can be comprised of:

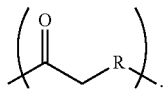

Formula I

The peptoid backbone subunit is comprised of peptoid submonomers. A peptoid submonomer can refer to the primary amine-R group conjugate (NH$_2$—R), which is reacted with a carbonyl group of the preceding backbone subunit to form a new peptide backbone subunit. In some instances, the peptoid submonomer can be referred to as a synthon.

In some instances the N subunits is at least 1, 2, 3, 4, 5 or more. In some instances the N subunits is 2.

Conjugated to the N peptoid subunits is an aromatic or non-aromatic ring structure where position A is always a carbon, but positions B-F can be either carbon or nitrogen. The aromatic ring can be comprised of:

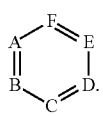

Formula II

In some instances the aromatic ring can be a 1,3,5-triazine ring with B, D, and F positions being nitrogens. In some instances the triazine ring is di-substituted at the C and E positions.

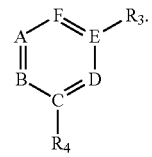

Formula III

In some instances the switchable affinity reagent has a backbone structure comprised of:

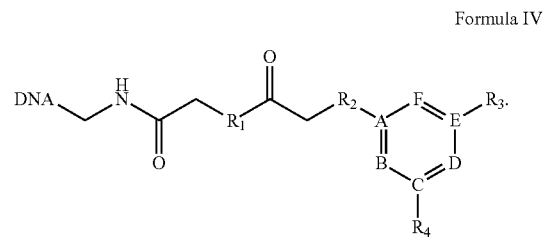

Formula IV

In some embodiments the switchable reagents comprises the backbone structure with R groups as described in Table 5. The R1-R4 groups in Table 5 correspond to the R1-R4 groups in Formulas I, III, or IV where one or more of the N—H bond(s) from the compounds in the table are converted to C—N bonds in the Formula. Accordingly, in various embodiments, the switchable reagents are the compounds described in Formulas I, III, or IV with the identity of the R groups as described in Table 5.

The peptoid switchable reagent can be used to purify target proteins from a mixture. In some instances the mixture is derived from a cellular lysate. In some instances the mixture of proteins is derived from non-animal sources. Non-limiting examples of non-animal sources include plants, funghi, bacteria, yeasts, algae, archaea, genetically modified organisms such as genetically modified bacteria or yeast, chemical or in vitro synthesis. In particular embodiments, the one or more target proteins are derived from plant sources. Any suitable plant can be used as a source of one or more target proteins for purification using one or more switchable affinity reagents. Non-limiting examples of plants that can be a source of the target proteins include abaca (Manila hemp); alfalfa; almond; anise seeds; apple; apricot; areca (betel nut); arracha; arrowroot; artichoke; asparagus; avocado; bajra (pearl millet); bambara groundnut; banana; barley; beans; beet, red; beet, sugar; bergamot; betel nut; black pepper; black wattle; blackberries of various species; blueberry; brazil nut; breadfruit; broad bean; broccoli; broom millet; broom sorghum; brussels sprouts; buckwheat; cabbage (red, white, savoy); cabbage, chinese; cacao (cocoa); cantaloupe; caraway seeds; cardamom; cardoon; carob; carrot; cashew nuts; cassava (manioc); castor bean; cauliflower; celeriac; celery; chayote; cherry (all varieties); chestnut; chickpea (gram pea); chicory; chili; cinnamon; citron; citronella; clementine; clove; clover (all varieties); cocoa (cacao); coconut; cocoyam; coffee; cola nut (all varieties); colza (rapeseed); corn (maize); corn (sweet); cotton (all varieties); cottonseed (all varieties); cowpea; cranberry; cress; cucumber; currants (all varieties); custard apple; dasheen; dates; drumstick tree; durra (sorghum); durum wheat; earth pea; edo (eddoe); eggplant; endive; fennel; fenugreek; fig; filbert (hazelnut); Pique; flax; flax seed oil (linseed); formio (New Zealand flax); garlic; geranium; ginger; gooseberry (all varieties); gourd; gram pea (chickpea); grape; grapefruit; grass esparto; grass, orchard; grass, sudan; groundnut (peanut); guava; guinea corn (sorghum); hazelnut (filbert); hemp; hempseed; henequen; henna; hop; horse bean; horseradish; hybrid maize; indigo; jasmine; jerusalem artichoke; jowar (sorghum); jute; kale; kapok; kenaf; kohlrabi; lavender; leek; lemon; lemon grass; lentil; lespedeza (all varieties); lettuce; lime, sour; lime, sweet; linseed; liquorice; litchi; loquat; lupine (all varieties); macadamia (Queensland nut); mace; maguey; maize; mandarin; mangel (fodder beet); mango; manioc (cassava); maslin (mixed cereals); medlar; melon; millet broom; millet, bajra; millet, bulrush; millet, finger; millet, foxtail; millet, japanese; millet, pearl (bajra, bulrush); millet, proso; mint (all varieties); mulberry (all varieties); mushrooms; mustard; nectarine; New Zealand flax (formio); niger seed; nutmeg; oats; oil palm; okra; olive; onion, green; opium; orange; ornamental plants; palm palmyra; palm, kernel oil; palm, oil; palm, sago; papaya (pawpaw); parsnip; pea; peach; peanut (groundnut); pear; pecan nut; pepper, black; persimmon; pigeon pea; pineapple; pistachio nut; plantain; plum; pomegranate; pomelo; poppy seed; potato; potato, sweet; prune; pumpkin; pyrethum; quebracho; queensland nut; quince; quinine; quinoa; radish; ramie; rapeseed (colza); raspberry (all varieties); red beet; redtop; rhea; rhubarb; rice; rose; rubber; rutabaga (swede); rye; ryegrass seed; safflower; sainfoin; salsify; sapodilla; satsuma (mandarin/tangerine); scorzonera black salsify; sesame; shea butter (nut); sisal; sorghum; sorghum, broom; sorghum, durra; sorghum, guinea corn; sorghum, jowar; sorghum, sweet; soybean; soybean hay; spelt wheat; spinach; squash; strawberry; sugar beet; sugarcane; sunflower; sunhemp; swede; sweet corn; sweet lime; sweet pepper; sweet potato; sweet sorghum; donax, energy cane, sorghum, other grasses, alfalfa, corn stover, kelp, other seaweeds, green matter ordinarily discarded from harvested plants, sugar cane leaves, leaves of trees, root crops such as cassava, sweet potato, potato, carrots, beets, turnips, plants from the legume family, such as, e.g., clover, peas such as cowpeas, english peas, yellow peas, green peas, beans such as, e.g., soybeans, fava beans, lima beans, kidney beans, garbanzo beans, mung beans, pinto beans, lentils, lupins, mesquite, carob, soy, and peanuts, coconut, vetch (vicia), stylo (stylosanthes), arachis, indigofera, acacia, leucaena, cyamopsis, and sesbania. One of skill in the art will understand that any organism in the plant kingdom may be used in the present invention.

In some instances the peptoid switchable reagent is used to purify Rubisco. Rubisco (Ribulose-1,5-bisphosphate carboxylase oxygenase) is an enzyme involved in the process of carbon fixation and is one of the most abundant proteins in plants. Rubisco can be isolated from, for example alfalfa, carrot tops, corn stover, sugar cane leaves, soybean leaves, switchgrass, miscanthus, energy cane, arundo donax, seaweed, kelp, algae or mustard greens.

The peptoid pH switchable reagents can bind Rubisco in base and release Rubisco in acid. In some embodiments the switchable reagents comprises the backbone structure with R groups as described in Table 1. The R1-R4 groups in Table 1 correspond to the R1-R4 groups in Formulas I, III, or IV where one or more of the N—H bond(s) from the compounds in the table are converted to C—N bonds in the Formula. Accordingly in various embodiments the switchable reagents are the compounds described in Formulas I, III, or IV with the identity of the R groups as described in Table 1.

TABLE 1

Peptoid pH switchable reagents that bind Rubisco in base and release Rubisco in acid comprise the backbone structure with R groups comprising:

| | R1 | R2 | R3 | R4 |
|---|---|---|---|---|
| pH switchable reagent 1 | 4-IODOBENZYLAMINE | 4-nitro-benzylamine | ISOAMYLAMINE | BENZYLAMINE |
| pH switchable reagent 2 | 4-PYRROLIDINOBUTYLAMINE | 3-ISOPROPOXYPROPYLAMINE | 2-amino-N-cyclopropyl-Acetamide | cyclopropylamine |
| pH switchable reagent 3 | 1-(3-AMINOPROPYL)PYRROLIDINE | N1-(2-aminoethyl)-N1-methylethane-1,2-diamine | DL-HOMOCYSTEINE THIOLACTONE | N-(3'-AMINOPROPYL)-2-PYRROLIDINONE |
| pH switchable reagent 4 | 2-(2-AMINOETHOXY)ETHANOL | 3-CHLOROANILINE | 9-AMINOFLUORENE | 2-amino-3-hydroxy-Butanoic acid |
| pH switchable reagent 5 | 3-(AMINOMETHYL)PYRIDINE | (1R,2R)-(−)-2-AMINO-1-PHENYL-1,3-PROPANEDIOL | 3,5-dimethyl-Phenylalanine | 3-(METHYLTHIO)-PROPYLAMINE |
| pH switchable reagent 6 | 4-(2-AMINOETHYL)-1-BENZYLPIPERIDINE | 2-(aminomethyl)pyridine | HOMOTAURINE | HOMOTAURINE |
| pH switchable reagent 7 | 4-(2-AMINOETHYL)MORPHOLINE | D-PHENYLALANINOL | BUTYLAMINE | 2-METHYLBUTYLAMINE | tangerine; tannia; tapioca (cassava); taro; tea; teff; timothy; tobacco; tomato; trefoil; triticale for fodder; tung tree; tree (all types) turnip; arena (Congo jute); vanilla; vetch for grain; walnut; watermelon; wheat; yam; yerba mate; corn, maize, oats, rice, wheat, barley, rye, triticale, teff, oilseeds including cottonseed, sunflower seed, safflower seed, crambe, camelina, mustard, rapeseed, leafy greens such as, e.g., lettuce, spinach, kale, collard greens, turnip greens, chard, mustard greens, dandelion greens, broccoli, cabbage, green matter not ordinarily consumed by humans, including biomass crops, including switchgrass, miscanthus, arundo The peptoid pH switchable reagents can bind Rubisco in acid and release Rubisco in base. In some embodiments the switchable reagents comprises the backbone structure with R groups as described in Table 2. The R1-R4 groups in Table 2 correspond to the R1-R4 groups in Formulas I, III, or IV where one or more of the N—H bond(s) from the compounds in the table are converted to C—N bonds in the Formula. Accordingly, in various embodiments, the switchable reagents are the compounds described in Formulas I, III, or IV with the identity of the R groups as described in Table 2.

TABLE 2

Peptoid pH switchable reagents that bind Rubisco in acid and release Rubisco in base comprise the backbone structure with R groups comprising:

| | | | | |
|---|---|---|---|---|
| pH switchable reagent 1 | N-(3-AMINOPROPYL)-MORPHOLINE | (R)-(+)-1-PHENYLETHYLAMINE | 2-ETHOXYETHYLAMINE | 2-METHYLBUTYLAMINE |
| pH switchable reagent 2 | N-(3-AMINOPROPYL)-MORPHOLINE | (1R,2R)-(−)-2-BENZYLOXYCYCLOPENTYLAMINE | 2-AMINO-1-METHOXYBUTANE | 2-METHYLBUTYLAMINE |
| pH switchable reagent 3 | (R)-1-(3-METHOXYPHENYL)-ETHYLAMINE | TRANS-4-AMINOCYCLOHEXANOL | BUTYLAMINE | 2-METHYLBUTYLAMINE |
| pH switchable reagent 4 | piperazine | 2-(dimethylamino)-4-Pyridinemethanamine | 2-(2-CHLOROPHENYL)-ETHYLAMINE | 2-AMINOETHYL ISOPROPYL ETHER |
| pH switchable reagent 5 | 3-AMINO-1-PROPANOL BENZYLAMINE | 2-(dimethylamino)-4-Pyridinemethanamine | 3,4,5-TRIMETHOXY- | 2-METHYLBUTYLAMINE |

In some instances the peptoid switchable reagent is used to purify Leghemoglobin. Leghemoglobin is a nitrogen or oxygen carrier and is produced in response to plant roots being infected with nitrogen-fixing bacteria. Leghemoglobin, is readily available as an unused by-product of commodity legume crops (eg., soybean, pea). The leghemoglobin in the roots of these crops in the US exceeds the myoglobin content of all the red meat consumed in the US.

Leghemoglobin can be obtained from a variety of plants. Various legumes species and their varieties, for example, Soybean, Fava bean, Lima bean, Cowpeas, English peas, Yellow peas, Lupine, Kidney bean, Garbanzo beans, Peanut, Alfalfa, Vetch hay, Clover, Lespedeza and Pinto bean, contain nitrogen-fixing root nodules in which leghemoglobin has a key role in controlling oxygen concentrations (for example root nodules from a pea plant).

The peptoid pH switchable reagents can bind leghemoglobin in base and release leghemoglobin in acid. In some embodiments the switchable reagents comprises the backbone structure with R groups as described in Table 3. The R1-R4 groups in Table 3 correspond to the R1-R4 groups in Formulas I, III, or IV where one or more of the N—H bond(s) from the compounds in the table are converted to C—N bonds in the Formula. Accordingly in various embodiments the switchable reagents are the compounds described in Formulas I, III, or IV with the identity of the R groups as described in Table 3.

TABLE 3

Peptoid pH switchable reagents that bind Leghemoglobin in base and release Leghemoglobin in acid comprise the backbone structure with R groups comprising:

| | | | | |
|---|---|---|---|---|
| pH switchable reagent 1 | N,N-bis(2-aminoethyl)ethane-1,2-diamine | 2-(4-CHLOROPHENYL)-ETHYLAMINE | N-(3-AMINOPROPYL)-MORPHOLINE | 2-(2-AMINOETHOXY)ETHANOL |
| pH switchable reagent 2 | 3,4-DICHLOROBENZYLAMINE | 1-(3-AMINOPROPYL)PYRROLIDINE | 1-phenylbutan-3-amine | 2-CHLOROBENZYLAMINE |
| pH switchable reagent 3 | 3-FLUORO-5-(TRIFLUOROMETHYL)-BENZYLAMINE | 2,4,6-TRIMETHYLANILINE | 3-FLUORO-5-(TRIFLUOROMETHYL)-BENZYLAMINE | indan-5-ylamine |
| pH switchable reagent 4 | 2-METHOXYETHYLAMINE | 5-METHOXYTRYPTAMINE | N1-(2-aminoethyl)-N1-methylethane-1,2-diamine | N,N,2,2-TETRAMETHYL-1,3-PROPANEDIAMINE |

The peptoid pH switchable reagents can bind leghemoglobin in acid and release leghemoglobin in base. In some embodiments the switchable reagents comprises the backbone structure with R groups as described in Table 4. The R1-R4 groups in Table 4 correspond to the R1-R4 groups in Formulas I, III, or IV where one or more of the N—H bond(s) from the compounds in the table are converted to C—N bonds in the Formula. Accordingly in various embodiments the switchable reagents are the compounds described in Formulas I, III, or IV with the identity of the R groups as described in Table 4.

TABLE 4

Peptoid pH switchable reagents that bind Leghemoglobin in acid and release Leghemoglobin in base comprise the backbone structure with R groups comprising:

| | | | | |
|---|---|---|---|---|
| pH switchable reagent 1 | 4-PYRROLIDINOBUTYLAMINE | 2-(1H-indol-3-yl)-ethanamine (tryptamine) | 2-CHLOROBENZYLAMINE | 2-AMINOETHYL ISOPROPYL ETHER |
| pH switchable reagent 2 | N1-(2-aminoethyl)-N1-methylethane-1,2-diamine | 2-(4-CHLOROPHENYL)-ETHYLAMINE | 8-Quinolinemethanamine | 2-AMINOETHYL ISOPROPYL ETHER |
| pH switchable reagent 3 | 3-FLUOROPHENETHYLAMINE | TRANS-4-AMINOCYCLOHEXANOL | 2-(2-AMINOETHYL)-1-METHYLPYRROLIDINE | 3-CHLORO-2,6-DIFLUOROBENZYLAMINE |

TABLE 4-continued

Peptoid pH switchable reagents that bind Leghemoglobin in acid and release
Leghemoglobin in base comprise the backbone structure with R groups comprising:

| | | | | |
|---|---|---|---|---|
| pH switchable reagent 4 | N,N,2,2-TETRAMETHYL-1,3-PROPANEDIAMINE | D-PHENYLALANINOL | 4-PYRROLIDINOBUTYLAMINE | 5-AMINOMETHYL-2-CHLOROPYRIDINE |
| pH switchable reagent 5 | N,N-DIMETHYL-1,3-PROPANEDIAMINE | 5-AMINOMETHYL-2-CHLOROPYRIDINE | 2-(4-nitro-phenyl)-ethylamine hydrochloride salt | HOMOTAURINE |

DNA-Programmed Combinatorial Chemistry (DPCC)

A library of switchable affinity reagents can be produced using a process termed DNA-programmed combinatorial chemistry; for example, as disclosed in Wrenn, et al. J Am Chem Soc. 2007 Oct. 31; 129(43): 13137-13143 or U.S. Pat. No. 7,479,472, each of which is hereby incorporated by reference in its entirety. DNA-programmed combinatorial chemistry can enable selection of an affinity reagent that has high and selective affinity for native features of a target protein from a combinatorial library of small molecules.

DNA-programmed combinatorial chemistry (DPCC) can be used to synthesize diverse combinatorial libraries of affinity reagents, wherein the affinity reagents comprise a small molecule compound attached to an encoding polynucleotide sequence that encodes a program for the synthesis of the small molecule compound from an array of precursors. The term "combinatorial library" can refer to a library of molecules containing a large number (e.g., between about $10^3$ and $10^{12}$) of different compounds. The compounds can be characterized by different sequences of subunits or precursors, or a combination of different sequences of side chains and linkages. The term "small molecule" can refer to small organic molecules that can have a common parent structure (e.g., a ring structure, a triazine, a peptoid, a peptide, etc.) and a plurality of different R group substituents or ring-structure modifications, each of which takes a variety of forms, e.g., different R groups. In one embodiment, small molecule compounds are non-oligomeric (that is, do not consist of sequences of repeating similar subunits). In one example, small molecule compounds can be similar in terms of basic structure and functional groups, but vary in such aspects as chain length, ring size or number, or patterns of substitution. In one embodiment, the precursors are amino acids. In another embodiment, the precursors are peptoids. In another embodiment, the precursors are L-peptides. In another embodiment, the precursors are D-peptides.

Strategy for Synthesis of Combinatorial Libraries

Encoded combinatorial chemical libraries can comprise a plurality of species of candidate affinity reagents. Affinity reagents can be bifunctional molecules comprising a small molecule compound and an encoding polynucleotide sequence, wherein the encoding polynucleotide sequence defines, and directs the synthesis of the corresponding small molecule compound.

Encoding Polynucleotide Sequence

In one embodiment, an affinity reagent comprises a small molecule compound and an encoding polynucleotide sequence that encodes a program for the synthesis of the small molecule compound. The encoding polynucleotide sequence can comprise one or more homology sequences. Each homology sequence can specify the addition of a specific precursor molecule. Homology sequences can be characterized by the following properties: (i) homology sequences can bind to their corresponding complementary nucleotide sequences (hereafter "complementary sequences") at a specified melting temperature (e.g. about 5° C., 10° C., 15° C., 20° C., 25° C., 30° C., 35° C., 40° C., 45° C., 50° C., 55° C., 60° C., 65° C., 70° C., 75° C., 80° C., 85° C., 90° C., 95° C., 100° C., or any included integer or fraction) under specified solution conditions and (ii) the homology sequences do not cross-hybridize efficiently with another of the 1536 sequences, or with the complement to any of the other 1536 sequences, at the specified melting temperature and specified solution conditions.

The number of homology sequences in an encoding polynucleotide sequence can be selected based upon a desired length of the small molecule compound. The number of homology sequences in the encoding polynucleotide sequence can be between about 1 and about 50; for example, about 1-50, 1-40, 1-30, 1-25, 1-20, 1-15, 1-10, 1-5, 5-50, 5-40, 5-30, 5-25, 5-20, 5-15, 5-10, 10-50, 10-40, 10-30, 10-25, 10-20, 10-15, 15-50, 15-40, 15-30, 15-25, 15-20, 20-50, 20-40, 20-30, 20-25, 25-50, 25-40, 25-30, 30-50, 30-40, 40-50, 3-6, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 homology sequences. In one example, the encoding polynucleotide sequence comprises about 5 homology sequences. In another example, the encoding polynucleotide comprises about 10 homology sequences. In another example, the encoding polynucleotide comprises about 15 homology sequences. The encoding polynucleotide sequence can comprise between about 3 and about 6 homology sequences; for example, about 3, 4, 5, or 6 homology sequences.

In one embodiment, a homology sequence can comprise between about 1 and about 50 nucleotides; for example about 1-50, 1-40, 1-30, 1-25, 1-20, 1-15, 1-10, 1-5, 5-50, 5-40, 5-30, 5-25, 5-20, 5-15, 5-10, 10-50, 10-40, 10-30, 10-25, 10-20, 10-15, 15-50, 15-40, 15-30, 15-25, 15-20, 20-50, 20-40, 20-30, 20-25, 25-50, 25-40, 25-30, 30-50, 30-40, 40-50, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides. In one embodiment, the homology sequences comprise about 10 nucleotides. In another embodiment, the homology sequences comprise about 20 nucleotides. In one embodiment, each homology sequence in the encoding polynucleotide sequence comprises a unique sequence. In another embodiment, two or more homology sequences in the encoding peptide can comprise the same sequence.

An encoding polynucleotide sequence can further comprise one or more spacer sequences. The number of spacer sequences can vary according to the number of homology sequences. In one embodiment, each homology sequence is separated by a spacer sequence. The spacer sequences can comprise between 1 and 50 nucleic acids; for example, about 1-50, 1-40, 1-30, 1-25, 1-20, 1-15, 1-10, 1-5, 5-50, 5-40, 5-30, 5-25, 5-20, 5-15, 5-10, 10-50, 10-40, 10-30, 10-25, 10-20, 10-15, 15-50, 15-40, 15-30, 15-25, 15-20, 20-50, 20-40, 20-30, 20-25, 25-50, 25-40, 25-30, 30-50, 30-40, 40-50, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides. In one embodiment, the spacer sequences comprise about 5 nucleic acids. In another embodiment, the spacer sequences comprise about 10 nucleic acids. In another embodiment, the spacer sequences comprise about 15 nucleic acids. In one embodiment, each spacer sequence comprises an identical nucleotide sequence. In another embodiment, two or more unique spacer sequences are used.

An encoding polynucleotide sequence can further comprise a chemical reaction site. In one embodiment, the chemical reaction site is located at the end, e.g. the 5' end, of the encoding polynucleotide sequence. In another embodiment, the chemical reaction site is located at the end, e.g. the 3' end, of the polynucleotide sequence. In one embodiment, the 5' alcohol of the 5' base of the nucleic acid tag is modified with a commercially available reagent which introduces a phosphate group tethered to a linear spacer, e.g., a 12-carbon and terminated with a primary amine group (e.g., Glen Research catalog #10-1912-xx or numerous other reagents which are available for introducing thiols or other chemical reaction sites into synthetic DNA). In this embodiment, the primary amine represents the chemical reaction site on which a small molecule compound is synthesized. Many different types of chemical reaction sites (in addition to primary amines) can be introduced at the 5' terminus of the encoding polynucleotide sequence. Exemplary chemical reaction sites include, but are not limited to, chemical components capable of forming amide, ester, urea, urethane, carbon-carbonyl bonds, carbon-nitrogen bonds, carbon-carbon single bonds, olefin bonds, thioether bonds, and disulfide bonds. In the case of enzymatic synthesis, co-factors may be supplied as are required for effective catalysis; for example, the phosphopantetheinyl group useful for polyketide synthesis.

Synthesis of Small Molecule Compounds

A split-and-recombine strategy, comprising two or more synthetic steps, can be utilized for synthesis of combinatorial libraries. A traditional split-and-recombine strategy for synthesis of combinatorial libraries has been described. Chen, et al., Methods in Enzymology 267:211-9 (1996); Ellman and Gallop, Curr Opin Chem Biol 2:317-319 (1998). For example, in a combinatorial synthesis consisting of i steps, for which j different chemical coupling reactions are performed at each step, $j^i$ compounds will be present in the final library. The traditional split and-recombine strategy is carried out using the following steps; (i) at the beginning of each of the i steps, the pool of solid tags is randomly split into j subsets, (ii) each of the j subsets of solid tags is subjected to a different chemical coupling step, and (iii) after the chemical coupling step, the subsets are recombined into a single pool. This recombined pool is again randomly divided into j subsets (specifically as in (i) above) at the beginning of the next step in the library synthesis. In the synthesis of peptide libraries, for example, the coupling step is the addition of an amino-acid active ester to a free amine group on the solid tag. Each of the j subsets is coupled to a different amino acid (e.g. alanine coupled to subset #1, arginine to subset #2, cysteine to subset #3 etc.). For example, a split-and-recombine synthesis of 10 synthetic steps, with 10 coupling reactions at each step, would yield a final library size of $10^{10}$.

A compound library can be split into subsets at each step of the split-and-recombine combinatorial synthesis by differential hybridization of an encoding polynucleotide sequence comprising one or more homology sequences to complementary sequences bound to a solid support (e.g., polystyrene beads). The complementary sequences to each homology sequence of the encoding polynucleotide sequence can be synthesized. In one embodiment, a 5' alcohol of the 5' base of the each complementary sequence is modified with a commercially available reagent that introduces a phosphate group tethered to a linear spacer (e.g., a linear spacer having six carbons and terminated with a thiol group (Glen Research catalog #10-1926-xx)). Each of the thiol-bearing complementary sequences can be immobilized, for example, through a thioether linkage to a macroporous resin (e.g., polystyrene, MPS; Biopore catalog #NH-2CM, L-970317) bearing electrophilic bromoacetamide groups. Thus a number of affinity resins result, each bearing a unique complementary sequence. Each of the affinity resins can be loaded into its own column. The columns can comprise luer-lock fittings at either end. The columns can be connected in a linear sequence.

A first split can be performed by contacting a library of encoding polynucleotide sequences with the previously described affinity resins. In one embodiment, the contacting can comprise pumping a high-salt aqueous solution containing the entire library of encoding polynucleotide sequences cyclically over a linear sequence of affinity columns under high stringency conditions see, e.g., Southern, E M et al., Nucl Acids Res. 22(8) 1368-1373 (1994), using a peristaltic pump and for a time sufficient for all of the encoding polynucleotide sequences to hybridize to the complementary sequences bound to the columns. The split can be completed by breaking the luer-lock linkages between the affinity columns. At this point the different encoding polynucleotide sequences have been divided into physically separate subsets on the basis of homology sequences contained with the encoding polynucleotide sequences.

Each subset of encoding polynucleotide sequences formed by hybridization as described supra can then be subjected to a different synthetic coupling reaction. The methods employed in the synthetic coupling reaction can vary according to the desired small molecule compound. For example, an amino terminus blocking group, e.g., fluorenylmethoxycarbonyl group (FMOC), which can be added and removed, can be used in the synthesis of a small molecule compound comprising peptide subunits.

An exemplary procedure to synthesize small molecule compounds comprising peptide or amino acid subunits or precursors is as follows: The encoding polynucleotide sequences bound to the affinity columns can be eluted off of the affinity columns with 10 mM NaOH and 0.005% Triton X-100. The polynucleotide sequences are transferred onto chemistry columns, e.g., hydroxyapatite resin columns (Bio-Rad Macro-Prep Ceramic Hydroxyapatite TYPE II catalog #1588200) with binding in 300 mM $CaCl_2$ or DEAE Sepharose fastflow (Pharmacia 17-0709-01) with binding in 10 mM acetate at pH 5.0 with 0.005% triton. The encoding polynucleotide sequences can remain non-covalently bound to the hydroxyapatite or sepharose resin in numerous organic solvents (e.g., DMF, acetonitrile, ethanol, and mixtures of those solvents with water). Thus organic reagents can be flowed over the columns and reacted with chemical reaction sites on the encoding nucleotide sequences in the same manner that conventional solid phase chemical synthesis is carried out. Accordingly, a different Fmoc-protected amino-acid preactivated with N[(1H-benzotriazol-1-yl) (dimethylamino) methylene]-N-methylmethanaminium tetrafluoroborate (TBTU) or as an N-hydroxy succinimide ester in DMF can be flowed over each hydroxyapatite or sepharose column, resulting in the acylation of the primary amines of the chemical reaction site on each of the hydroxyapatite or sepharose columns with an Fmoc-protected amino acid [Albericio, F. and Carpino L A, Methods in Enymology 289:104-26 (1997)]. Following acylation, the Fmoc group can removed from the newly added amino acid by flowing a piperidine/DMF solution over the hydroxyapatite or sepharose columns, thus presenting a new primary amine ready for the next coupling step.

An exemplary procedure to synthesize small molecule compounds comprising peptoid subunits or precursors is as follows: The encoding polynucleotide sequences bound to the affinity columns are transferred onto chemistry columns (e.g., DEAE-sepharose columns). Chemistry columns can be washed with DEAE bind buffer (10 mM acetic acid, 0.005% TritonX100), water, methanol, or a combination thereof. The chemistry columns can then be incubated one or more times (e.g., 2 times) with 150 mM DMT-MM (4-(4, 6-Dimethoxy-1,3,5-triazin-2-yl)-4-methylmorpholinium chloride) and 100 mM sodium chloroacetate in distilled methanol for a period of time of about 20 minutes. The chemistry columns can then be washed with methanol, and incubated with a solution containing a desired peptoid subunit. The column can be microwaved for about 20 seconds one or more times during the peptoid incubation; for example, 1, 2, 3, 4, 5, 6, or more times. The chemistry column can then be washed, for example, with DMSO (dimethylsulfoxide), DEAE bind buffer, or a combination thereof.

An entire affinity reagent library can be synthesized by carrying out alternate rounds of library splitting and chemical and/or biochemical coupling to each subset of encoding nucleotide sequences.

Modifications to Generate Switchable Affinity Reagents

The described methods of generating affinity reagent libraries can be modified in order to generate switchable affinity reagents, wherein the switchable affinity reagents comprise a small molecule compound and an encoding polynucleotide sequence. The small molecule compound can be synthesized from subunit or precursors, as described supra. In one embodiment, the precursors can be chosen to bias the synthesis toward a family of molecules with a pKa about 7, so that they can be neutrally charged at about pH 9 and positively charged at about pH 5. The affinity reagents can be incubated with a crude mixture of non-specific proteins (e.g., cell lysates from *Escherichia coli*), which can eliminate molecules with non-specific affinity for proteins. The remaining library can then be incubated at a binding pH (e.g., about pH 9) with the target protein, attached to a solid support. Affinity reagents that fail to bind to the target protein can be washed away. Then the buffer pH can be adjusted to a release pH (e.g., about pH 5) and the bound affinity reagents that elute can be collected. It should be understood that the stated pH values are provided merely as examples and that a variety of binding and release pH combinations are contemplated.

This selection can be reiterated to obtain progressively greater enrichment of the affinity reagents that perform best in the selection (e.g., binding at about pH 9 and eluting at about pH 5). The selected pool of affinity reagents can be identified by sequencing the attached DNA molecules, resynthesized, and further characterized for their specificity to the target protein and performance under actual purification conditions. Any number of reiterations can be employed to select the affinity reagents; for example, 1, 2, 3, 4, 5, 6, 7, 8, 9, 10, 11, 12, 13, 14, 15, 16, 17, 18, 19, 20, or more reiterations can be performed.

Note that the specific properties of the affinity reagents, including the manner in which affinity for the targeted protein is controlled (either by pH or other changes in conditions) may vary from the above ¬ the methods for discovering them and for using them to purify a target protein can be indifferent to the specifics of the affinity switch.

Target Proteins, Compounds, or Molecules

A target protein, compound, or molecule can be any protein, compound, or molecule that has industrial value, clinical effect, or environmental effect. Target proteins, compounds, or molecules can be used as food ingredients. Target proteins can be enzymes (e.g., industrial enzymes). Target proteins, compounds, or molecules can be used as therapeutic agents; for example, target proteins can include antibodies or other proteins that can be used to treat a disease or disorder such as cancer. Target proteins, compounds, or molecules can include analytes for a diagnostic test or other clinical use.

A target protein, compound, or molecule can also be a protein, compound or molecule whose presence in a mixture is undesirable. For example, a target protein, compound or molecule can be a toxin or an allergen; for example the target protein could be hordein in a fermented barley beverage whose removal would render the beer "gluten free". A target protein, compound, or molecule can contribute to an undesirable taste, odor, or visual appearance in a product such as a food product. A target protein, compound, or molecule can be target protein, compound, or molecule (e.g., enzyme) whose activity decreases the stability of a desired material; for example, the target protein could be an RNAse in a cell extract wherein RNA is the desired material. A switchable affinity reagent can be used to remove undesirable target proteins, compounds or molecules from a mixture comprising a desired material.

The target proteins or molecules can be used to produce a consumable; for example, a meat substitute food product. The consumable can be for human consumption. The consumable can be approved by suitable regulatory authorities. The consumables can be sold in grocery stores or prepared in restaurants, similar to already existing human foods. The consumable can be for animal consumption. The consumable can be food for domestic animals; for example, farm animals (e.g., cows, sheep, pigs, goats, horses, chickens, turkeys, etc.) or pets (e.g., cats, dogs, ferrets, rabbits, hamsters, guinea pigs, mice, fish, birds, etc.). The consumable can be food for wild animals (e.g., foxes, wolves, bears, great cats, primates, rodents, crocodiles, alligators, iguanas, lizards, snakes, tortoises, turtles, frogs, fish, etc.).

Target proteins can comprise animal proteins. Non-limiting examples of animal sources of proteins include humans, monkeys, farm animals, mammals, birds, reptiles and insects.

Target proteins can comprise proteins derived from non-animal sources. Non-limiting examples of non-animal sources include plants, funghi, bacteria, yeasts, algae, archaea, genetically modified organisms such as genetically modified bacteria or yeast, chemical or in vitro synthesis.

Target proteins can comprise plant proteins. Target proteins can be purified from crude solutions derived from plant material. Non-limiting examples of plant proteins include RuBisCO (ribulose-1,5-bisphosphate carboxylase oxygenase), leghemoglobin, non-symbiotic hemoglobin, ribosomes, cytoplasmic actin, and seed storage proteins. In one example, the target proteins comprise RuBisCO (alternatively "Rubisco" or "rubisco"). In another example, the target proteins comprise a leghemoglobin. In another example, the target proteins comprise a non-symbiotic hemoglobin. In one example, the target proteins comprise a ribosomal protein. In another example, the target proteins comprise a cytoplasmic actin. In another example, the target protein comprise seed storage proteins; for example, an albumin, a conalbumin, a glutenin, a gliadin, a glutelin, a gluten, a hordein, a prolamine, a phaseolin, a secalin, a triticeae gluten, or a zein. In another example, the target proteins are selected from the group consisting of leghemoglobin, non-symbiotic hemoglobin, hemoglobin, myoglobin, chlorocruorin, erythrocruorin, neuroglobin, cytoglobin, protoglobin, truncated 2/2 globin, HbN, cyanoglobin, HbO, Glb3, and cytochromes, Hell's gate globin I, bacterial hemoglobins, ciliate myoglobins, flavohemoglobins, ribosomal proteins, actin, hexokinase, lactate dehydrogenase, fructose bisphosphate aldolase, phosphofructokinases, triose phosphate isomerases, phosphoglycerate kinases, phosphoglycerate mutases, enolases, pyruvate kinases, proteases, lipases, amylases, glycoproteins, lectins, mucins, glyceraldehyde-3-phosphate dehydrogenases, pyruvate decarboxylases, actins, translation elongation factors, histones, ribulose-1,5-bisphosphate carboxylase oxygenase (rubisco), ribulose-1,5-bisphosphate carboxylase oxygenase activase (rubisco activase), albumins, glycinins, conglycinins, globulins, vicilins, conalbumin, gliadin, glutelin, gluten, glutenin, hordein, prolamin, phaseolin (protein), proteinoplast, secalin, extensins, triticeae gluten, collagens, zein, kafirin, avenin, dehydrins, hydrophilins, late embyogenesis abundant proteins, natively unfolded proteins, any seed storage protein, oleosins, caloleosins, steroleosins or other oil body proteins, vegetative storage protein A, vegetative storage protein B, moong seed storage 8S globulin, pea globulins, pea albumins, or combinations thereof In another example the target proteins are selected from the group consisting of leghemoglobin, non-symbiotic hemoglobin, hemoglobin, myoglobin, chlorocruorin, erythrocruorin, neuroglobin, cytoglobin, protoglobin, truncated 2/2 globin, HbN, cyanoglobin, HbO, Glb3, and cytochromes, Hell's gate globin I, bacterial hemoglobins, ciliate myoglobins, flavohemoglobins, ribosomal proteins, actin, hexokinase, lactate dehydrogenase, fructose bisphosphate aldolase, phosphofructokinases, triose phosphate isomerases, phosphoglycerate kinases, phosphoglycerate mutases, enolases, pyruvate kinases, proteases, lipases, amylases, glycoproteins, lectins, mucins, glyceraldehyde-3-phosphate dehydrogenases, pyruvate decarboxylases, actins, translation elongation factors, histones, ribulose-1,5-bisphosphate carboxylase oxygenase (rubisco), ribulose-1,5-bisphosphate carboxylase oxygenase activase (rubisco activase), albumins, glycinins, conglycinins, globulins, vicilins, conalbumin, gliadin, glutelin, gluten, glutenin, hordein, prolamin, phaseolin (protein), proteinoplast, secalin, extensins, triticeae gluten, collagens, zein, kafirin, avenin, dehydrins, hydrophilins, late embyogenesis abundant proteins, natively unfolded proteins, any seed storage protein, oleosins, caloleosins, steroleosins or other oil body proteins, vegetative storage protein A, vegetative storage protein B, moong seed storage 8S globulin, pea globulins, pea albumins, or combinations thereof Any mixture of proteins can be used as a source of one or more target proteins for purification using one or more switchable affinity reagents. In some instances the mixture is derived from a cellular lysate. In some instances the mixture of proteins is derived from non-animal sources. Non-limiting examples of non-animal sources include plants, funghi, bacteria, yeasts, algae, archaea, genetically modified organisms such as genetically modified bacteria or yeast, chemical or in vitro synthesis. In particular embodiments, the one or more target proteins are derived from plant sources. Any suitable plant can be used as a source of one or more target proteins for purification using one or more switchable affinity reagents. Non-limiting examples of plants that can be a source of the target proteins include abaca (Manila hemp); alfalfa; almond; anise seeds; apple; apricot; areca (betel nut); arracha; arrowroot; artichoke; arundo donax: asparagus; avocado; bajra (pearl millet); bambara groundnut; banana; barley; beans; beet, red; beet, sugar; bergamot; betel nut; black pepper; black wattle; blackberries of various species; blueberry; brazil nut; breadfruit; broad bean; broccoli; broom millet; broom sorghum; brussels sprouts; buckwheat; cabbage (red, white, savoy); cabbage, chinese; cacao (cocoa); cantaloupe; caraway seeds; cardamom; cardoon; carob; carrot; cashew nuts; cassava (manioc); castor bean; cauliflower; celeriac; celery; chayote; cherry (all varieties); chestnut; chickpea (gram pea); chicory; chili; cinnamon; citron; citronella; clementine; clove; clover (all varieties); cocoa (cacao); coconut; cocoyam; coffee; cola nut (all varieties); colza (rapeseed); corn (maize); corn (sweet); cotton (all varieties); cottonseed (all varieties); cowpea; cranberry; cress; cucumber; currants (all varieties); custard apple; dasheen; dates; drumstick tree; durra (sorghum); durum wheat; earth pea; edo (eddoe); eggplant; endive; fennel; fenugreek; fig; filbert (hazelnut); Pique; flax; flax seed oil (linseed); formio (New Zealand flax); garlic; geranium; ginger; gooseberry (all varieties); gourd; gram pea (chickpea); grape; grapefruit; grass esparto; grass, orchard; grass, sudan; groundnut (peanut); guava; guinea corn (sorghum); hazelnut (filbert); hemp; hempseed; henequen; henna; hop; horse bean; horseradish; hybrid maize; indigo; jasmine; jerusalem artichoke; jowar (sorghum); jute; kale; kapok; kenaf; kohlrabi; lavender; leek; lemon; lemon grass; lentil; lespedeza (all varieties); lettuce; lime, sour; lime, sweet; linseed; liquorice; litchi; loquat; lupine (all varieties); macadamia (Queensland nut); mace; maguey; maize; mandarin; mangel (fodder beet); mango; manioc (cassava); maslin (mixed cereals); medlar; melon; millet broom; millet, bajra; millet, bulrush; millet, finger; millet, foxtail; millet, japanese; millet, pearl (bajra, bulrush); millet, proso; mint (all varieties); miscanthus; mulberry (all varieties); mushrooms; mustard; nectarine; New Zealand flax (formio); niger seed; nutmeg; oats; oil palm; okra; olive; onion, green; opium; orange; ornamental plants; palm palmyra; palm, kernel oil; palm, oil; palm, sago; papaya (pawpaw); parsnip; pea; peach; peanut (groundnut); pear; pecan nut; pepper, black; persimmon; pigeon pea; pineapple; pistachio nut; plantain; plum; pomegranate; pomelo; poppy seed; potato; potato, sweet; prune; pumpkin; pyrethum; quebracho; queensland nut; quince; quinine; quinoa; radish; ramie; rapeseed (colza); raspberry (all varieties); red beet; redtop; rhea; rhubarb; rice; rose; rubber; rutabaga (swede); rye; ryegrass seed; safflower; sainfoin; salsify; sapodilla; satsuma (mandarin/tangerine); scorzonera—black salsify; sesame; shea butter (nut); sisal; sorghum; sorghum, broom; sorghum, durra; sorghum, guinea corn; sorghum, jowar; sorghum, sweet; soybean; soybean hay; spelt wheat; spinach; squash; strawberry; sugar beet; sugarcane; sunflower; sunhemp; swede; sweet corn; sweet lime; sweet pepper; sweet potato; sweet sorghum; tangerine; tannia; tapioca (cassava); taro; tea; teff; timothy; tobacco; tomato; trefoil; triticale for fodder; tung tree; tree (all types) turnip; arena (Congo jute); vanilla; vetch for grain; walnut; watermelon; wheat; yam; yerba mate; corn, maize, oats, rice, wheat, barley, rye, triticale, teff, oilseeds including cottonseed, sunflower seed, safflower seed, crambe, camelina, mustard, rapeseed, leafy greens such as, e.g., lettuce, spinach, kale, collard greens, turnip greens, chard, mustard greens, dandelion greens, broccoli, cabbage, green matter not ordinarily consumed by humans, including biomass crops, including switchgrass, miscanthus, arundo donax, energy cane, sorghum, other grasses, alfalfa, corn stover, kelp, other seaweeds, green matter ordinarily discarded from harvested plants, sugar cane leaves, leaves of trees, root crops such as cassava, sweet potato, potato, carrots, beets, turnips, plants from the legume family, such as, e.g., clover, peas such as cowpeas, english peas, yellow peas, green peas, beans such as, e.g., soybeans, fava beans, lima beans, kidney beans, garbanzo beans, mung beans, pinto beans, lentils, lupins, mesquite, carob, soy, and peanuts, coconut, vetch (vicia), stylo (stylosanthes), arachis, indigofera, acacia, leucaena, cyamopsis, and sesbania. One of skill in the art will understand that any organism in the plant kingdom may be used in the present invention.

Methods for Purifying Target Proteins, Compounds, or Molecules

The present disclosure provides numerous methods for the purification of one or more target proteins, compounds or molecules using one or more switchable affinity reagents. The methods can comprise the step of (a) applying a composition comprising one or more target proteins, compounds, or molecules to a substrate comprising one or more switchable affinity reagents at a binding pH such that the target proteins, compounds, or molecules bind to the switchable affinity reagents; and (b) applying a solution at a release pH to the substrate comprising the one or more switchable affinity reagents such that the one or more target proteins, compounds, or molecules are released from the one or more switchable affinity reagents. The methods can further comprise a washing step wherein a wash solution is applied to the substrate comprising the one or more switchable affinity reagents bound to the one or more target proteins, wherein the wash solution is at or near the binding pH. The wash step can be used to remove one or more undesirable components (e.g., undesirable proteins, contaminants, etc.). The methods disclosed herein can be used to obtain a pure, concentrated solution of the one or more target proteins.

Immobilization of pH Switchable Reagent on Substrate

The switchable affinity reagents can be immobilized on a substrate (e.g., on beads, a solid support or a semi-solid support). The switchable affinity reagents can be packed into a column or other suitable container. The pH switchable reagent can be conjugated to a substrate such as a bead. Substrate, e.g. beads, can be made of styrene, polystyrene, iron oxide, agarose, or sepharose. Substrate, e.g. beads, can be magnetic or paramagnetic. Substrate, e.g. beads, can be coated with silica or high density functional groups, such as carboxyl groups, aldehyde groups, or N-hydroxysuccinimide-ester (NHS) groups. A collection of conjugated substrate, e.g. beads, in a slurry can form a resin.

The pH switchable reagent can be conjugated to a substrate, e.g. beads. pH switchable reagents can be conjugated to substrate using chemicals such as N-ethylmaleimide (NEM), N-hydroxysuccinimide (NHS) and other imidoesters, other chemical crosslinkers such as 1-ethyl-3-(-3-dimethylaminopropyl) (EDC, EDAC) carbodiimide hydrochloride, and N',N'-dicyclohexyl carbodiimide (DCC), iodoacetate and alpha-halocarbonyl compounds or any chemicals which react with primary amines or thiols.

Resins can comprise cross-linked beaded agarose, cross-linked bisacrylamide and azlactone, or polyethylene glycol. Resins can be microporous or macroporous. The binding capacity of resins can be measure in terms of the milligram amount of protein bound per milliliter amount of resin. Resins can be packed into columns for large scale affinity chromatography purification of a target protein from a cellular lysate.

In one example, a column purification can be performed wherein a crude solution comprising the target proteins, compounds, or molecules are run through a column comprising beads or resin comprising one or more switchable affinity reagents. The crude solution can be at a binding pH (e.g., between about 7 and about 11, e.g., about 9). In this example, other components of the crude solution can pass through the column and can be collected and/or disposed. The crude solution can be run over the column one or more times. Running the crude solution over the column two or more times can increase the amount of the target proteins, compounds, or molecules that are purified from the crude solution. In another example, a batch purification can be performed wherein beads comprising one or more switchable affinity reagents can be added to a crude solution comprising one or more target proteins, compounds, or molecules. The crude solution can be at a binding pH (e.g., between about 7 and about 11, e.g., about 9). Following an incubation period with optional mixing, the beads can be collected and removed from the crude solution, along with any target proteins bound to the switchable affinity reagents. Both column and batch purification methods can comprise one or more wash steps, wherein the wash steps are performed with a solution that is at or near the binding pH (e.g., between about 7 and about 11, e.g., about 9). In both column and batch purifications, the one or more target proteins, compounds, or molecules can be released from the switchable affinity reagents using a solution at a release pH (e.g., between about 3 and about 7, e.g., about 5). Both column and batch purification methods can be used to produce pure concentrated solutions of the target proteins, compounds, or molecules.

Purification of plant-derived target proteins using a pH switchable reagent is designed to occur on massively large scale. Isolation of high fructose corn syrup, antibiotics or industrial proteins can occur in columns >4 m in diameter. These columns are often used for process development and manufacturing. Columns used for purifying plant target proteins using pH switchable reagents can be up to 1, 2, 3, 4, 5, 6, 7, 8, 9, or 10 times the size of current largest columns. The amount of target protein recovered can be at least 0.1, 0.5, 1, 5, 10, 20, 50, 100, 200, 500, 1000, 5000, 10000, 50000, 100000 or more grams. The concentration of the recovered target protein can be at least 0.1 mg/mL, 0.5 mg/mL, 1 mg/mL, 5 mg/mL, 10 mg/mL, 20 mg/mL, 50 mg/mL, 100 mg/mL, 200 mg/mL, 500 mg/mL.

Purity of the target sample will be assessed with standard protein purity detection techniques such as SDS page, mass spectrometry, spectroscopy and other molecular biology techniques well known to those skilled in the art.

In some instances the pH switchable reagent will leach off the column and be carried into the target protein sample which is used in downstream processes to produce a consumable food product, suggesting that the consumable food product may contain minute quantities of the pH switchable reagent. In some instances, the amount of leached pH switchable reagent and/or pH switchable reagent resin will be at most 1, 100, 500, 1000, 2000, 5000 parts per million target protein. In some instances the amount of leached pH switchable reagent and/or pH switchable reagent resin will represent at most $10^{-9}$, $10^{-8}$, $10^{-7}$, $10^{-6}$, $10^{-5}$, $10^{-4}$, $10^{-3}$, 0.01, 0.05, 0.1, 0.5, 1, 2, 3, 4, 5, 6, 7, 8, 9, 10 percent weight/volume of the purified target protein composition. In some instances, the amount of leached pH switchable reagent and/or pH switchable reagent resin will represent at most 0.001, 0.005, 0.01, 0.05, 0.1, 0.5, 1, 5, 10, 20, 50, 100, 150, 200, 250, 300, 350, 400, 450, 500, 550, 600, 650, 700, 750, 800, 850, 900, 1000 parts per billion (ppb). In some instances the purified target protein will represent more than 10, 20, 30, 40, 50, 60, 70, 80, 85, 90, 91, 92, 93, 94, 95, 96, 97, 98, 98.5, 99, 99.5, 99.9, 99.95 percent of the weight/volume of the purified target protein composition. In some instances the purified target protein is increased by a factor of 2 or more, 3 or more, 5 or more, 10 or more, 20 or more, 50 or more, 100 or more or 1000 or more relative to the source material from which the specified protein was isolated.

A pure target protein can be substantially free of celluloses and complex polysaccharides. Cellulose is the polysaccharide responsible for the structural integrity of the plant cell wall. Celluloses are only partially digestible by humans and may not be desirable in a consumable product. Celluloses can comprise lignin, hemicellulose, and cellulose. Complex polysaccharides can also be found in the walls of plant cells. Complex polysaccharides may not be desirable in a consumable product. Complex polysaccharides can comprise arabinose, xylose, arabinoxylans, cellulose, lignin, hemicellulose, chitin, pectin, amylose, or amylopectins.

A pure target protein can be substantially free of colorants and/or odorants, or contain trace amounts of colorants and/or odorants. Colorants may include anions, cations, salts, metals, alkali metals, metalloids, or transition elements. Colorants may be of a type related to chlorophylls such as chlorins, chlorophyll a, chlorophyll b, chlorophyll c1, chlorophyll c2, chlorophyll d, and chlorophyll f. In some instances, the amount colorant and/or odorant will be at most 1, 100, 500, 1000, 2000, 5000, 10000, 100000 parts per million target protein. In some instances the amount of colorant and/or odorant will represent at most 0.05, 0.1, 0.5, 1, 2, 3, 4, 5, 6, 7, 8, 9, 10 percent weight/volume of the purified target protein composition. In some instances the purified target protein will represent more than 90, 91, 92, 93, 94, 95, 96, 97, 98, 98.5, 99, 99.5, 99.9, 99.95 percent of the weight/volume of the purified target protein composition.

Methods for Removing Contaminants or Hazards from a Mixture

The present disclosure also provides numerous methods for removing one or more undesirable components (e.g., contaminants, toxins, hazards, etc.) from a mixture using switchable affinity reagents, wherein the switchable affinity reagents specifically bind to the undesirable components under a first set of conditions (e.g., a binding pH) and do not bind or bind less strongly under a second set of conditions. The switchable affinity reagents can be bound to a solid support or substrate such as a bead or a resin. Beads or resins comprising one or more switchable affinity reagents can be used in column or batch purifications. In one example, a mixture comprising one or more undesirable components is applied to a column, wherein the column is packed with beads or resin comprising one or more switchable affinity reagents, wherein the switchable affinity specifically bind to the one or more undesirable components under a first set of conditions (e.g., a binding pH) and do not bind, or bind less strongly under a second set of conditions (e.g., a release pH). Prior to running the mixture over the column, it can be adjusted to the first set of conditions (e.g. the binding pH) and then the mixture that passes through the column will have all, substantially all, or a portion of the undesired components removed. The mixture can be passed through the column one or more additional times in order to further deplete the mixture of the undesirable components. A second solution under the second set of conditions (e.g., the release pH) can be passed over the column to regenerate the beads or resin by releasing the undesirable components from the switchable affinity reagents. Such method can be useful, for example, for removing toxins from an environment. Such methods can also be useful for removing allergens or other undesirable components from a mixture.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Examples

Example 1: Preparation of DNA Libraries

To make DNA Libraries 3072 40mer oligonucleotides were synthesized using standard phosphoramidite chemistry. The 5' 20 bases of each oligonucleotide consisted of a noncoding region sequence, while the 3' 20 bases consisted of a codon sequence. 1536 of the oligos were "forward" reads, 1536 of the oligos were "anti-sense". The oligonucleotides were divided into 8 subpools from each of 5 sets exclusive to A-type codons (A001-A384 forward, and A001'-A384' antisense), B-type codons (B1-B384 forward, and B001'-B384' antisense), and so forth through E-type codons. Oligos were diluted to 4.5 µM concentration in 1× T4 polynucleotide kinase (PNK) buffer (Fermentas). Oligos were heated to 95° C. 5 min to denature, and then cooled to room temperature over an hour to hybridize. The 8 subpools from each of the 5 sets were pooled to make 5 pools. The resulting constructs are comprised of 2 oligos that have annealed along the first 20 bases of their 3' ends but are un-annealed at their 5' 20 bases. The constructs are phosphorylated with T4 PNK (Fermentas) with 3.2 µM oligonucleotide, 1 mM ATP, 1×PNK buffer, 0.11 units/µl PNK in 750 µl volume, reacted for 8 hours at 37° C. The reactions are concentrated to 250 ul by n-butanol extraction and ten ethanol precipitated with $MgCl_2$ to 10 mM and 1.25 ml ethanol. Pellets are resuspended in 200 ul TAE and purified by agarose gel electrophoresis. Equimolar amounts from each coding region are combined for ligation. Ligation reactions were conducted on 15 ug of purified constructs with 5% PEG4000, 1× T4 ligase buffer, 0.1 units of DNA ligase/ul in 500 ul at 37 C overnight. The reaction was phenol/chloroform extracted, concentrated by n-butanol extraction to 300 ul and precipitated by isopropanol. Pellets were dissolved in 30 ul H2O and 30 ul formamide loading dye were added. The ligation reactions of assembled library were purified on a 5% TBE formamide (40%)—urea (7M) denaturing gel. After gel purification, the library was PCR amplified.

Example 2: Construction of Hybridization Array and Attachment of Oligos

Hybridization arrays were constructed using Delrin polymer. Holes were cut into the array using an Epilog36 ext laser cutter. The array contains azido-sepharose which allows the oligos to be clicked onto the array. To attach oligos to the array, the array was placed into a chembot (Array-to-384-well plate adapter) to facilitate performing reactions on the array in a feature-specific manner. Attachment of the oligos to the array was effected by a click chemistry reagent solution which was added rapidly to the oligos and then the mixture of click reagents and oligos were rapidly added to the appropriate wells on the chembot. The reaction was run for 15 min at room temp, whereupon the reaction solution was spun through the array, out of the chembot, into a receiver plate. The reaction mix was re-added to the chembot wells, and reacted for another 15 min. During that 15 min reaction, a second aliquot of ascorbate was added to each well of the receiver plate. The reaction mix was spun through the array, out of the chembot, and into the receiver plate where it mixed with the fresh ascorbate. Two more 15 minute reactions were done, with spin-outs and reloads between them. After the reaction completed, the array was washed by pouring a "quench" buffer into the shallow reservoir atop the chembot and pulling the buffer through on the vacuum manifold 6 or 7 times. The "quench" buffer is 100 mM Tris pH 8, 10 mM EDTA pH8, 0.005% triton x-100, 0.02% SDS. The array was stored in Array Storage Buffer: 10 mM Tris, 1 mM EDTA, 150 mM NaCl, 0.01% azide, 0.005% triton x-100.

Example 3: Conversion of dsDNA into Hybridization-Ready DNA (hrDNA)

PCR was used to amplify the dsDNA library. The PCR products were in vitro transcribed using T7 RNA polymerase. RNA was purified using lithium chloride precipitation. Library RNA was reverse transcribed. The cDNA was purified using sodium acetate precipitation. The library was incubated with Zip oligos that are complementary to the conserved regions of DNA. Hydrolysis of the RNA leaves ssDNA, and annealing of Zip oligos results in a construct that is intermittently single- and double-stranded, and which is ready for sorting by hybridization on an array. hrDNA is recovered using centrifugal concentrators.

Example 4: Binding of Library hrDNA to Hybridization Array

The library of hrDNA was sorted on the array by hybridization in 2×SSC, +15 mM Tris pH7.4+0.005% Triton X100, 0.02% SDS, 0.05% sodium azide for 60 hours at 37° C. Unhybridized DNA was eluted off the arrays by washing in 40 ml hybridization buffer for 20-30 minutes. A second wash buffer of 12.5% Hybridization Buffer in 40 ml dH2O+ 0.005% triton+0.02% SDS was incubated with the array at 37° C. for 20-30 minutes. DNA was eluted into 384-well plates placing the array in the chembot, adding 30 ul 10 mM NaOH+0.005% TritonX100+0.02% SDS, to each well of the chembot, incubating for 8-10 minutes and spinning out of the chembot into a 384-well plate. The elute buffer was neutralized with 9 ul of 1M HOAc and 9 ul of 1M Tris pH 7.4 to each well.

Example 5: Peptoid Coupling Chemical Reaction

The array-bound hrDNA library was chemically translated via a peptoid coupling step. 20-30 ul of settled DEAE resin was added to each well of a filter plate and washed with a bind buffer of 10 mM acetic acid, 0.005% Triton X-100 mixed 1:1 with water. Eluted hrDNA was added to the plate, which was then washed with 1×80 ul bind buffer, 2×80 ul dH2O, and 3×80 ul dry MeOH. Acetylation reagents were prepared immediately before use as below (the exact amounts will vary depending on how much settled DEAE resin was used to capture the DNA. Use at least 125% as much reaction solution volume as settled resin. The numbers below give >40 ul of acetylation reaction mix per well and are sufficient for any amount of resin less than ~35 ul.): Sodium chloroacetate, 10 ml of 200 mM stock solution (233 mg) DMT-MM-Cl, (4-(4,6-Dimethoxy-1,3,5-triazin-2-yl)-4-methylmorpholinium chloride) 10 ml of 300 mM stock solution (830 mg). Equal volumes of the 2 stock solutions were rapidly combined, vortexed, and aliquoted into the wells with alacrity, 30 ul per well, reacted for 15 minutes, and drained on the vacuum manifold. The samples were washed twice with 1×80 ul dry MeOH and once with 3×80 ul dry MeOH, 1×80 ul dH2O, 3×80 ul DMSO.

Example 6: Triazine Coupling Chemical Reaction 5 ul saturated $K_2B_4O_7$ (pH9.2) was added to a 384-well plate. Array was washed in hybridization buffer 3×20 min at 37° C. DNA was eluted with 3×30 ul of elute buffer into the library elution plate. 6 ul of ~250 mM cyanuric chloride was added to a separate 384-well plate. The reaction was initiated by transferring DNA from the Library Elution Plate to the plate containing the cyanuric chloride and was reacted for 1 hr at 4° C. The triazine adduct was reacted with amine synthons. A filter plate was loaded with 25 ul DEAE resin and washed with 4×80 ul DEAE bind buffer. 11 ul of synthons from the R1 or R2 sections of Table 5 were added to a separate, synthon mix plate. 56 ul of the cyanuric chloride reactions was added to each well of the filter plate, mixed, incubated for 5 minutes, and drained. This was repeated until all the material from the cyanuric chloride reaction plate was transferred to the filter plate. The DEAE resin in the filter plate was immediately washed with 2×80 ul ACN, 2×80 ul dH2O. The filter plate was stoppered and 45 ul 75 mM $K_2B_4O_7$ pH 9.5 was added to it. Synthon mixes from the synthon mix plate were added to the filter plate and reacted for 16 hrs at 4° C. The DEAE resin was washed with 3×80 ul ACN, 2×80 ul dH2O. DNA was eluted by adding 6 ul of 1M Tris pH7.4 to each well of a new plate labeled DEAE Elution Plate and 4×33 ul DEAE Elute Buffer (containing 50 mM NaOH) with 4 min incubations between elutions. The eluents were concentrated in centrifugal concentrators. The hrDNA was then re-sorted by hybridization as described above. The second synthesis step was performed by adding 9 ul saturated borate, the eluted hrDNA, and 30 ul of synthon mixes (such as synthons drawn from the R3 section of Table 5) to each well of a receiver plate. The plate was reacted for 6 hours at 80° C. Synthons with lower solubilities were precipitated with 45 ul of dH2O via mixing for 60 seconds, and centrifugation at 569×g for 30 minutes. Supernatants were removed from the plate and combined. DNA was eluted three times from the receiver plate with 33 ul of Elution Buffer (1.5M NaCl+0.05M NaOH+0.005% triton)

Example 7: Converting hrDNA to Double-Stranded DNA

The eluted hrDNA was desalted by alcohol precipitation and made double stranded in a single cycle PCR reaction. The cycle conditions included an initial denaturation of 7 min at 95° C., an anneal step of 1 min at 57° C., and an extension of 10 min at 72° C. PCR products were purified by alcohol precipitations.

Example 8: Selections of Switchable Affinity Reagent

A 10 mM Bis-Tris-Propane buffer was made. To each pH of buffer Tween (to 0.5%) (and 0.05% triton), tRNA (60 ng/ul), and BSA (0.2 mg/ml) was added. 50 ul streptavidin beads were added to 500 ul biotinylated E. coli Lysate. Separately, 12 ul of streptavidin beads were added to biotinylated rubisco and leghemoglobin. The lysate was passed through a column, washed with 4 mL of the appropriate pH buffer and eluted with 60 ul of the appropriate pH buffer. The pH of library was adjusted by adding BTP to 20 mM, and KCl to 100 mM. The library was added to the lysate beads, incubated for 15 minutes, and poured on the column. The flow-through was collected. 3 mM EDTA and protease inhibitor was added to 380 ul of the lysate mix (66 uM, ~250 fold over library). Then the library was added and incubated for 5 minutes. The mixes were pH'd as appropriate with 200 mM BTP with the addition of KCl to 100 mM. Separately, target-bead mixes were poured through a column and washed with 1 ml appropriate pH buffer. Bead-bound targets were eluted with 100 ul appropriate buffer (5 column volumes) and added to a mix of library and E. coli Lysate, and incubated for 20 min. Mixes were poured through columns, washed with 6000 ul of appropriate buffer, and collected in 1200 ul aliquots. A final wash was performed with 60 ul and collected separately. Elution was performed with a 1×60 ul aliquot, a 1×40 ul aliquot, and a 1×60 ul aliquot. Beads were pressed off the column with 60 ul pH7.5 buffer.

Example 9: Identity of the Switchable Reagent

The libraries were screened for binding to two proteins: leghemoglobin and rubisco. The ligands were selected for binding at low pH and release at high pH and also for high pH binding and low pH release. After screening a number of molecules were enriched and the following ligand structures were chosen for further testing.

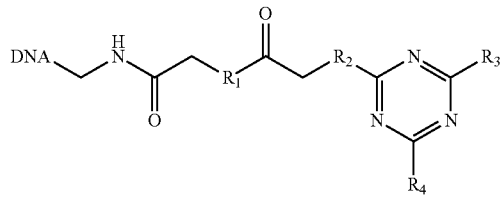

Example 10: Sequencing of Library Members Surviving Selection and Analysis of Selection Products Those library members surviving the selection were analyzed by deep sequencing. The selected library was amplified by PCR. The number of rounds of PCR required varied with the stringency of the selection, more stringently selected libraries requiring more cycles. Sequencing was performed by commercial providers of DNA sequencing services using the Illumina MiSeq instrument. Libraries were prepared in accordance with the individual provider's instructions. Sequencing yielded ~15 million DNA sequences per experiment.

The DNA sequences were analyzed statistically to determine which library members in the selections were capable of binding the target proteins in a pH dependent manner. Library members were considered to be selected if they met the following criteria: the relative abundance of sequences encoding a library member must be enriched after a selection, the number of different genes encoding a library member must be greater than 1, the library member must be part of a family of library members with similar chemical structures that were also enriched, the library member must not also be enriched in a negative control selection performed in the absence of a desired target, the library member must not also be enriched in selections for other targets, the library member must not be enriched in selections for the same target under other condition (eg. a library member enriched in a selection binding Rubisco in acid and eluting in base, is not considered if it is also seen to be enriched in a selection binding Rubisco in base and eluting in acid). Exemplary results are summarized in Tables 1-4 above.

Prophetic Example 11: Generation of Switchable Reagent for Purification of Target Protein Selected molecules will be conjugated to a set of beads and will be mixed to create four different resins. The resins will be packed into four large columns which can have a column cross section diameter of greater than 4 meters. These columns are often used for process development and manufacturing.

Prophetic Example 12: Purification of Rubisco and Leghemoglobin

The resins described in Example 11 will be used to purify a target protein by the column purification method. Columns containing pH switchable reagents that bind to the target protein Rubisco will be used to purify rubisco. Similarly, columns containing pH switchable reagents that bind to the target protein leghemoglobin will be used to purify leghemoglobin. The mixture of proteins will be flowed onto the column in a buffer with a first pH conducive for binding Rubisco or Leghemoglobin to the resin. The column will be washed in a similar buffer to remove non-specifically binding proteins. To elute the protein from the column, the column will be washed in a buffer with a second pH conducive for releasing the target protein from the resin. The collected protein will be subjected to further processes downstream for producing a consumable food product.

TABLE 5

Synthon table

Chemical Diversity Elements For $R_1$

2-PHENYLPROPYLAMINE, 4-METHYLBENZYLAMINE, 2-PHENYLETHANAMINE, BENZYLAMINE, 3-PHENYLPROPYLAMINE, 4-(2-AMINOMETHYL)BENZENESULFONAMIDE, 2-METHYLBUTYLAMINE,

TABLE 5-continued

Synthon table

ISOAMYLAMINE, ISOBUTYLAMINE, BUTYLAMINE, PROPARGYLAMINE,
PIPERAZINE, ETHYLAMINE, 1-AMINO-3,3-DIETHOXYPROPANE, 4-AMINO-2-
METHYL-1-BUTANOL, 5-AMINO-1-PENTANOL, ACETAMIDE, 2-AMINO-N-
CYCLOPROPYL-1-AMINO-2-BUTANOL, N,N-BIS(2-AMINOETHYL)ETHANE-1,2-
DIAMINE, N,N,2,2-TETRAMETHYL-1,3-PROPANEDIAMINE, N,N-DIETHYL-1,3-
PROPANEDIAMINE, N1-(2-AMINOETHYL)-N1-METHYLETHANE-1,2-DIAMINE, N,N-
DIMETHYL-1,3-PROPANEDIAMINE, 4-(DIFLUOROMETHOXY)BENZYLAMINE, 2-N-
PROPOXYETHYLAMINE, 2-METHOXYETHYLAMINE, N-TERT-BUTOXYCARBONYL-
3-AMINOPROPANAMINE, 3-ISOPROPOXYPROPYLAMINE, 3-
(METHYLTHIO)PROPYLAMINE, 2-AMINOETHYL ISOPROPYL ETHER, 4-BROMO-2-
FLUOROBENZYLAMINE, 4-IODOBENZYLAMINE, 4-BROMOBENZYLAMINE, 2-(4-
NITRO-PHENYL)-ETHYLAMINE, 3-FLUORO-5-(TRIFLUOROMETHYL)BENZYLAMINE,
4-NITRO-BENZYLAMINE, 3-BROMOBENZYLAMINE, 3-CHLORO-2,6-
DIFLUOROBENZYLAMINE, 3,4-DICHLOROBENZYLAMINE, 4-
(TRIFLUOROMETHYL)BENZYLAMINE, 2-(3-CHLOROPHENYL)ETHYLAMINE, 2-(4-
CHLOROPHENYL)ETHYLAMINE, 3-CHLOROBENZYLAMINE, 2-
CHLOROBENZYLAMINE, 3-FLUOROPHENETHYLAMINE, 4-
FLUOROPHENETHYLAMINE, 3-FLUOROBENZYLAMINE,
TETRAHYDROFURFURYLAMINE, 4-(2-AMINOETHYL)-1-BENZYLPIPERIDINE, (2,2-
DIMETHYL-[1,3]-DIOXOLAN-4-YL)-METHYLAMINE, N-(3-
AMINOPROPYL)MORPHOLINE, 4-(2-AMINOETHYL)MORPHOLINE, 2-(2-
AMINOETHYL)-1-METHYLPYRROLIDINE, 4-(AMINOMETHYL)PIPERIDINE, 2-
(AMINOMETHYL)-1-ETHYLPYRROLIDINE, 4-PYRROLIDINOBUTYLAMINE, 1-(3-
AMINOPROPYL)PYRROLIDINE, 1-(3-AMINOPROPYL)-4-METHYLPIPERAZINE, N-(3'-
AMINOPROPYL)-2-PYRROLIDINONE, ETHYL 4-AMINO-1-
PIPERIDINECARBOXYLATE, ETHANONE, 2-AMINO-1-(4-MORPHOLINYL)-3-
AMINOPROPANE-1,2-DIOL, 3-AMINOPROPIONITRILE, 3-AMINO-1-PROPANOL, 2-(2-
AMINOETHOXY)ETHANOL, 2-(1H-INDOL-3-YL)ETHANAMINE (TRYPTAMINE), 3-(2-
AMINOETHYL)PYRIDINE, 1H-INDOLE-2-METHANAMINE, ACETAMIDE, 2-AMINO-N-
(1-METHYLETHYL)-, 2-(2-METHOXYPHENYL)ETHYLAMINE, 2-
(AMINOMETHYL)PYRIDINE, 4-(2-AMINOETHYL)PYRIDINE, 2-
THIOPHENEMETHYLAMINE, 4-(AMINOMETHYL)PYRIDINE, 3-
(AMINOMETHYL)PYRIDINE, 3-BROMO-4-METHOXYPHENETHYLAMINE, 3-
FURANMETHANAMINE, 2-QUINOLINEMETHANAMINE, HOMOPIPERAZINE,
PROPANAMIDE, 3-AMINO-N-METHYL-, 2-(2-FURYLMETHYLTHIO)ETHANAMINE, 4-
(2-AMINOETHYL)BENZENESULFONAMIDE, 5-AMINOMETHYL-2-CHLOROPYRIDINE,
5-METHOXYTRYPTAMINE, N-ACETYLETHYLENEDIAMINE, S-(2-
AMINOETHYL)ISOTHIOURONIUM BROMIDE, HOMOTAURINE, (R)-1-(3-
METHOXYPHENYL)ETHYLAMINE, 2-(3,4-DIMETHOXYPHENYL)ETHYLAMINE, 3-
METHOXYPHENETHYLAMINE, 2-(4-METHOXYPHENYL)ETHYLAMINE, 4-
METHOXYBENZYLAMINE, 2-PHENOXYETHYLAMINE, 2-METHOXYBENZYLAMINE,
3-METHOXYBENZYLAMINE

Chemical Diversity Elements for $R_2$

2-PHENYLPROPYLAMINE, 4-METHYLBENZYLAMINE, 2-PHENYLETHANAMINE,
BENZYLAMINE, 3-PHENYLPROPYLAMINE, 4-(2-
AMINOMETHYL)BENZENESULFONAMIDE, 2-METHYLBUTYLAMINE,
ISOAMYLAMINE, ISOBUTYLAMINE, BUTYLAMINE, PROPARGYLAMINE,
PIPERAZINE, ETHYLAMINE, 1-AMINO-3,3-DIETHOXYPROPANE, 4-AMINO-2-
METHYL-1-BUTANOL, 5-AMINO-1-PENTANOL, ACETAMIDE, 2-AMINO-N-
CYCLOPROPYL-, 1-AMINO-2-BUTANOL, N,N-BIS(2-AMINOETHYL)ETHANE-1,2-
DIAMINE, N,N,2,2-TETRAMETHYL-1,3-PROPANEDIAMINE, N,N-DIETHYL-1,3-
PROPANEDIAMINE, N1-(2-AMINOETHYL)-N1-METHYLETHANE-1,2-DIAMINE, N,N-
DIMETHYL-1,3-PROPANEDIAMINE, 4-(DIFLUOROMETHOXY)BENZYLAMINE, 2-N-
PROPOXYETHYLAMINE, 2-METHOXYETHYLAMINE, N-TERT-BUTOXYCARBONYL-
3-AMINOPROPANAMINE, 3-ISOPROPOXYPROPYLAMINE, 3-
(METHYLTHIO)PROPYLAMINE, 2-AMINOETHYL ISOPROPYL ETHER, 4-BROMO-2-
FLUOROBENZYLAMINE, 4-IODOBENZYLAMINE, 4-BROMOBENZYLAMINE, 2-(4-
NITRO-PHENYL)-ETHYLAMINE, 3-FLUORO-5-(TRIFLUOROMETHYL)BENZYLAMINE,
4-NITRO-BENZYLAMINE, 3-BROMOBENZYLAMINE, 3-CHLORO-2,6-
DIFLUOROBENZYLAMINE, 3,4-DICHLOROBENZYLAMINE, 4-
(TRIFLUOROMETHYL)BENZYLAMINE, 2-(3-CHLOROPHENYL)ETHYLAMINE, 2-(4-
CHLOROPHENYL)ETHYLAMINE, 3-CHLOROBENZYLAMINE, 2-
CHLOROBENZYLAMINE, 3-FLUOROPHENETHYLAMINE, 4-
FLUOROPHENETHYLAMINE, 3-FLUOROBENZYLAMINE,
TETRAHYDROFURFURYLAMINE, 4-(2-AMINOETHYL)-1-BENZYLPIPERIDINE, (2,2-
DIMETHYL-[1,3]-DIOXOLAN-4-YL)-METHYLAMINE, N-(3-
AMINOPROPYL)MORPHOLINE, 4-(2-AMINOETHYL)MORPHOLINE, 2-(2-
AMINOETHYL)-1-METHYLPYRROLIDINE, 4-(AMINOMETHYL)PIPERIDINE, 2-
(AMINOMETHYL)-1-ETHYLPYRROLIDINE, 4-PYRROLIDINOBUTYLAMINE, 1-(3-
AMINOPROPYL)PYRROLIDINE, 1-(3-AMINOPROPYL)-4-METHYLPIPERAZINE, N-(3'-
AMINOPROPYL)-2-PYRROLIDINONE, ETHYL 4-AMINO-1-
PIPERIDINECARBOXYLATE, ETHANONE, 2-AMINO-1-(4-MORPHOLINYL)-, 3-
AMINOPROPANE-1,2-DIOL, 3-AMINOPROPIONITRILE, 3-AMINO-1-PROPANOL, 2-(2-
AMINOETHOXY)ETHANOL, 2-(1H-INDOL-3-YL)ETHANAMINE (TRYPTAMINE), 3-(2-
AMINOETHYL)PYRIDINE, 1H-INDOLE-2-METHANAMINE, ACETAMIDE, 2-AMINO-N-
(1-METHYLETHYL)-, 2-(2-METHOXYPHENYL)ETHYLAMINE, 2-
(AMINOMETHYL)PYRIDINE, 4-(2-AMINOETHYL)PYRIDINE, 2-

TABLE 5-continued

Synthon table

THIOPHENEMETHYLAMINE, 4-(AMINOMETHYL)PYRIDINE, 3-(AMINOMETHYL)PYRIDINE, 3-BROMO-4-METHOXYPHENETHYLAMINE, 3-FURANMETHANAMINE, 2-QUINOLINEMETHANAMINE, HOMOPIPERAZINE, PROPANAMIDE, 3-AMINO-N-METHYL-, 2-(2-FURYLMETHYLTHIO)ETHANAMINE, 4-(2-AMINOETHYL)BENZENESULFONAMIDE, 5-AMINOMETHYL-2-CHLOROPYRIDINE, 5-METHOXYTRYPTAMINE, N-ACETYLETHYLENEDIAMINE, S-(2-AMINOETHYL)ISOTHIOURONIUM BROMIDE, HOMOTAURINE, (R)-1-(3-METHOXYPHENYL)ETHYLAMINE, 2-(3,4-DIMETHOXYPHENYL)ETHYLAMINE, 3-METHOXYPHENETHYLAMINE, 2-(4-METHOXYPHENYL)ETHYLAMINE, 4-METHOXYBENZYLAMINE, 2-PHENOXYETHYLAMINE, 2-METHOXYBENZYLAMINE, 3-METHOXYBENZYLAMINE, (Z)-4-CHLORO-2-BUTEN-1-AMINE, 2-(1-CYCLOHEXENYL)ETHYLAMINE, 3-METHOXYPROPYLAMINE, 3-ETHOXYPROPYLAMINE, 3-N-PROPOXYPROPYLAMINE, 2-ETHOXYETHYLAMINE, 3-IODOBENZYLAMINE, 3-(TRIFLUOROMETHYL)BENZYLAMINE, 4-(4-FLUOROPHENOXY)BENZYLAMINE, 3,4-METHYLENEDIOXYBENZYLAMINE, 8-QUINOLINEMETHANAMINE, 4-PYRIDINEMETHANAMINE, 2-(DIMETHYLAMINO)-, 2-AMINOETHYL HYDROGEN SULFATE, AMINOMETHANESULFONIC ACID, 3,4,5-TRIMETHOXYBENZYLAMINE, DL-1-(1-NAPHTHYL)ETHYLAMINE, (S)-(−)-1-(4-METHYLPHENYL)ETHYLAMINE, (S)-(−)-BETA-METHYLPHENETHYLAMINE, (R)-(−)-1-AMINOINDAN, (S)-(−)-1-PHENYLETHYLAMINE, (R)-(+)-1-PHENYLETHYLAMINE, 1-PHENYLBUTAN-3-AMINE, D-PHENYLALANINOL, (1R,2S)-1-AMINO-2-INDANOL, 2-AMINO-3,3-DIMETHYLBUTANE, 1,3-DIMETHYLBUTYLAMINE, SEC-BUTYLAMINE, ISOPROPYLAMINE, 2-AMINO-1-METHOXYBUTANE, (S)-2-AMINO-1-PHENYLETHANOL, (S)-(+)-2-AMINO-1-PENTANOL, (R)-(−)-2-AMINO-1-BUTANOL, L-LEUCINAMIDE, CYCLOPENTYLAMINE, CYCLOPROPYLAMINE, TRANS-4-AMINOCYCLOHEXANOL, (1S,2S)-(+)-2-BENZYLOXYCYCLOHEXYLAMINE, (1R,2R)-(−)-2-BENZYLOXYCYCLOPENTYLAMINE, 2-(2-CHLOROPHENYL)ETHYLAMINE, 2-FLUOROPHENETHYLAMINE, (1R,2R)-(−)-2-AMINO-1-(4-NITROPHENYL)-1,3-PROPANEDIOL, 4-AMINOTETRAHYDROPYRAN, DL-HOMOCYSTEINE THIOLACTONE, DL-α-AMINO-ε-CAPROLACTAM, INDAN-5-YLAMINE, 4-AMINOPYRIDINE, N-(3-AMINOPROPYL)-N-METHYLANILINE, 2-FLUOROETHANAMINE, ALPHA-PHENYLGLYCINONITRILE, (1R,2R)-(−)-2-AMINO-1-PHENYL-1,3-PROPANEDIOL, BETA ALANINE NAPTHYLAMIDE, L-LEUCINE-4-NITROANILIDE, 2-AMINO-3-METHYL-3-SULFANYLBUTANOIC ACID, (S)-(−)-1-(3-METHOXYPHENYL)ETHYLAMINE, (S)-(−)-1-(4-METHOXYPHENYL)ETHYLAMINE, TRANS-2,5-DIMETHYLPIPERAZINE, 9-AMINOFLUORENE, 2,4,6-TRIMETHYLANILINE, 2,4-DIMETHYLANILINE, 3,5-DIMETHYL ANILINE, 2,5-DIMETHYLANILINE, 2-METHYLANILINE, 2,6-DIETHYLANILINE, 3-ISOPROPYLANILINE, 4-ISOPROPYLANILINE, m-AMINOBENZOYLAMINE, 4-AMINOBENZAMIDE, 3-NITROANILINE, 2,6-DIFLUOROANILINE, 3',4'-DIFLUOROANILINE, 3-CHLOROANILINE, 2-CHLOROANILINE, 2-FLUORO-ANILINE, 4-FLUOROANILINE, 3,4-METHYLENEDIOXY-1-AMINOBENZENE, 2-AMINOPYRAZINE, 3-AMINOPYRIDINE, 2-AMINOPYRIDINE, 4-METHYL-1,3-THIAZOL-2-AMINE, 2-AMINOPYRIMIDINE, 5-AMINO-1H-TETRAZOLE, 4-ETHOXYANILINE, 2-(METHYLMERCAPTO)ANILINE, 2-ETHOXYANILINE, o-ANISIDINE, 4-AMINO-1-BUTANOL

Chemical Diversity Elements for $R_3$

2-PHENYLPROPYLAMINE, 4-METHYLBENZYLAMINE, 2-PHENYLETHANAMINE, BENZYLAMINE, 3-PHENYLPROPYLAMINE, 4-(2-AMINOMETHYL)BENZENESULFONAMIDE, 2-METHYLBUTYLAMINE, ISOAMYLAMINE, ISOBUTYLAMINE, BUTYLAMINE, PROPARGYLAMINE, PIPERAZINE, ETHYLAMINE, 4-AMINO-2-METHYL-1-BUTANOL, 5-AMINO-1-PENTANOL, ACETAMIDE, 2-AMINO-N-CYCLOPROPYL-, 1-AMINO-2-BUTANOL, N,N-BIS(2-AMINOETHYL)ETHANE-1,2-DIAMINE, N,N,2,2-TETRAMETHYL-1,3-PROPANEDIAMINE, N,N-DIETHYL-1,3-PROPANEDIAMINE, N1-(2-AMINOETHYL)-N1-METHYLETHANE-1,2-DIAMINE, N,N-DIMETHYL-1,3-PROPANEDIAMINE, 4-(DIFLUOROMETHOXY)BENZYLAMINE, 3-(METHYLTHIO)PROPYLAMINE, 4-BROMO-2-FLUOROBENZYLAMINE, 4-BROMOBENZYLAMINE, 2-(4-NITRO-PHENYL)-ETHYLAMINE, 3-FLUORO-5-(TRIFLUOROMETHYL)BENZYLAMINE, 4-NITRO-BENZYLAMINE, 3-BROMOBENZYLAMINE, 3-CHLORO-2,6-DIFLUOROBENZYLAMINE, 3,4-DICHLOROBENZYLAMINE, 4-(TRIFLUOROMETHYL)BENZYLAMINE, 2-(3-CHLOROPHENYL)ETHYLAMINE, 3-CHLOROBENZYLAMINE, 2-CHLOROBENZYLAMINE, 3-FLUOROPHENETHYLAMINE, 4-FLUOROPHENETHYLAMINE, TETRAHYDROFURFURYLAMINE, 4-(2-AMINOETHYL)-1-BENZYLPIPERIDINE, (2,2-DIMETHYL-[1,3]-DIOXOLAN-4-YL)-METHYLAMINE, N-(3-AMINOPROPYL)MORPHOLINE, 4-(2-AMINOETHYL)MORPHOLINE, 2-(2-AMINOETHYL)-1-METHYLPYRROLIDINE, 4-(AMINOMETHYL)PIPERIDINE, 2-(AMINOMETHYL)-1-ETHYLPYRROLIDINE, 4-PYRROLIDINOBUTYLAMINE, 1-(3-AMINOPROPYL)-4-METHYLPIPERAZINE, N-(3'-AMINOPROPYL)-2-PYRROLIDINONE, ETHYL 4-AMINO-1-PIPERIDINECARBOXYLATE, ETHANONE, 2-AMINO-1-(4-MORPHOLINYL)-, 3-AMINOPROPANE-1,2-DIOL, 3-AMINOPROPIONITRILE, 3-AMINO-1-PROPANOL, 2-(2-AMINOETHOXY)ETHANOL, 2-(1H-INDOL-3-YL)ETHANAMINE (TRYPTAMINE), 3-(2-AMINOETHYL)PYRIDINE, 1H-INDOLE-2-METHANAMINE, ACETAMIDE, 2-AMINO-N-(1-METHYLETHYL)-, 2-(2-METHOXYPHENYL)ETHYLAMINE, 2-(AMINOMETHYL)PYRIDINE, 4-(2-AMINOETHYL)PYRIDINE, 4-(AMINOMETHYL)PYRIDINE, 3-(AMINOMETHYL)PYRIDINE, 3-BROMO-4-

TABLE 5-continued

Synthon table

METHOXYPHENETHYLAMINE, 3-FURANMETHANAMINE, 2-
QUINOLINEMETHANAMINE, HOMOPIPERAZINE, PROPANAMIDE, 3-AMINO-N-
METHYL-, 2-(2-FURYLMETHYLTHIO)ETHANAMINE, 4-(2-
AMINOETHYL)BENZENESULFONAMIDE, 5-METHOXYTRYPTAMINE, N-
ACETYLETHYLENEDIAMINE, (R)-1-(3-METHOXYPHENYL)ETHYLAMINE, 2-(3,4-
DIMETHOXYPHENYL)ETHYLAMINE, 2-(4-METHOXYPHENYL)ETHYLAMINE, 4-
METHOXYBENZYLAMINE, 2-PHENOXYETHYLAMINE, 2-METHOXYBENZYLAMINE,
3-METHOXYBENZYLAMINE, (Z)-4-CHLORO-2-BUTEN-1-AMINE, 2-(1-
CYCLOHEXENYL)ETHYLAMINE, 3-METHOXYPROPYLAMINE, 3-
ETHOXYPROPYLAMINE, 3-N-PROPOXYPROPYLAMINE, 2-ETHOXYETHYLAMINE, 3-
IODOBENZYLAMINE, 3-(TRIFLUOROMETHYL)BENZYLAMINE, 4-(4-
FLUOROPHENOXY)BENZYLAMINE, 3,4-METHYLENEDIOXYBENZYLAMINE, 8-
QUINOLINEMETHANAMINE, 4-PYRIDINEMETHANAMINE, 2-(DIMETHYLAMINO)-, 2-
AMINOETHYL HYDROGEN SULFATE, AMINOMETHANESULFONIC ACID, 3,4,5-
TRIMETHOXYBENZYLAMINE, DL-1-(1-NAPHTHYL)ETHYLAMINE, (S)-(–)-1-(4-
METHYLPHENYL)ETHYLAMINE, 1-PHENYLBUTAN-3-AMINE, D-
PHENYLALANINOL, (1R,2S)-1-AMINO-2-INDANOL, 2-AMINO-3,3-
DIMETHYLBUTANE, 1,3-DIMETHYLBUTYLAMINE, 2-AMINO-1-METHOXYBUTANE,
(S)-2-AMINO-1-PHENYLETHANOL, (S)-(+)-2-AMINO-1-PENTANOL, L-
LEUCINAMIDE, CYCLOPENTYLAMINE, CYCLOPROPYLAMINE, TRANS-4-
AMINOCYCLOHEXANOL, (1S,2S)-(+)-2-BENZYLOXYCYCLOHEXYLAMINE, (1R,2R)-(–)-
2-BENZYLOXYCYCLOPENTYLAMINE, 2-(2-CHLOROPHENYL)ETHYLAMINE, 2-
FLUOROPHENETHYLAMINE, (1R,2R)-(–)-2-AMINO-1-(4-NITROPHENYL)-1,3-
PROPANEDIOL, 4-AMINOTETRAHYDROPYRAN, DL-HOMOCYSTEINE
THIOLACTONE, DL-ALPHA-AMINO-EPSILON-CAPROLACTAM, INDAN-5-YLAMINE,
4-AMINOPYRIDINE, 2-(AMINOMETHYL)PIPERIDINE, 1-(3-AMINOPROPYL)-2-
PIPECOLINE, BENZENEPROPANOIC ACID, β-(AMINOMETHYL)-, BENZENEACETIC
ACID, A-(AMINOMETHYL)-, BENZOIC ACID, 2-(AMINOMETHYL)-, 6-
AMINOCAPROIC ACID, PENTANOIC ACID, 5-AMINO-, CYCLOHEXANECARBOXYLIC
ACID, 4-(AMINOMETHYL)-, (2S)-4-AMINO-2-HYDROXY-BUTYRIC ACID, N-(3-
AMINOPROPYL)-N-METHYLANILINE, TYRAMINE, PHENOL, 3-(AMINOMETHYL)-, 3-
METHOXYTYRAMINE, 2-FLUOROETHANAMINE, 3-AMINOPYRROLIDINE, 4-
AMINOPIPERIDINE, PHENYLALANINE, 3,5-DIMETHYL-, GLUTAMIC ACID, D-
PHENYLALANINE, 3-FLUORO-, BENZENEACETIC ACID, A-AMINO-4-FLUORO-,
TYROSINE, 3-FLUORO-, 4-PYRIDINEPROPANOIC ACID, A-AMINO-, (αR)-,
ASPARAGINE, ALPHA-PHENYLGLYCINONITRILE, (1R,2R)-(–)-2-AMINO-1-PHENYL-
1,3-PROPANEDIOL, BETA ALANINE NAPTHYLAMIDE, L-LEUCINE-4-
NITROANILIDE, 2-AMINO-3-METHYL-3-SULFANYLBUTANOIC ACID, 1,2,3,4-
TETRAHYDRO-1-NAPHTHYLAMINE, (S)-(–)-1-(3-METHOXYPHENYL)ETHYLAMINE,
(S)-(–)-1-(4-METHOXYPHENYL)ETHYLAMINE, trans-2,5-DIMETHYLPIPERAZINE, cis-2,
6 DIMETHYLPIPERAZINE, 3-PYRROLIDINECARBOXYLIC ACID, 1H-IMIDAZOLE, 1-
(3-PYRROLIDINYL)-, PYRROLIDINE, 3-(METHYLSULFONYL)-, 3-
PYRROLIDINECARBOXAMIDE, 9-AMINOFLUORENE, 2,6-DIETHYLANILINE, META-
AMINOBENZOYLAMINE, 3-NITROANILINE, 3,4-METHYLENEDIOXY-1-
AMINOBENZENE, 2-AMINOPYRAZINE, 4-ETHOXYANILINE, 1H-INDOL-5-OL, 3-(2-
AMINOETHYL)-, D-PHENYLALANINE, GLUTAMINE, BENZENEPROPANOIC ACID, B-
AMINO-3,4-DIHYDROXY-, BUTANOIC ACID, 2-AMINO-4,4,4-TRIFLUORO-,
BUTANOIC ACID, 2-AMINO-3-HYDROXY-, 3-THIOPHENEPROPANOIC ACID, α-
AMINO-, 3-THIOPHENEACETIC ACID, α-AMINO-, 2-MORPHOLINEACETIC ACID,
BENZOIC ACID, 4-AMINO-3-HYDROXY-, 1H-PYRAZOLE-3-CARBOXYLIC ACID, 5-
AMINO-, 4-AMINO-1-BUTANOL, 4-DIMETHYLAMINOBENZYLAMINE Chemical Diversity Elements for $R_4$ 2-PHENYLPROPYLAMINE, 4-METHYLBENZYLAMINE, 2-PHENYLETHANAMINE,
BENZYLAMINE, 3-PHENYLPROPYLAMINE, 4-(2-
AMINOMETHYL)BENZENESULFONAMIDE, 2-METHYLBUTYLAMINE,
ISOAMYLAMINE, ISOBUTYLAMINE, BUTYLAMINE, PROPARGYLAMINE, (Z)-4-
CHLORO-2-BUTEN-1-AMINE, 2-(1-CYCLOHEXENYL)ETHYLAMINE, 3-
METHOXYPROPYLAMINE, 3-ETHOXYPROPYLAMINE, 3-N-
PROPOXYPROPYLAMINE, 2-ETHOXYETHYLAMINE, 3-IODOBENZYLAMINE, 3-
(TRIFLUOROMETHYL)BENZYLAMINE, 4-(4-FLUOROPHENOXY)BENZYLAMINE, 3,4-
METHYLENEDIOXYBENZYLAMINE, 8-QUINOLINEMETHANAMINE, 4-
PYRIDINEMETHANAMINE, 2-(DIMETHYLAMINO)-, PIPERAZINE, ETHYLAMINE, 1-
AMINO-3,3-DIETHOXYPROPANE, 4-AMINO-2-METHYL-1-BUTANOL, 5-AMINO-1-
PENTANOL, ACETAMIDE, 2-AMINO-N-CYCLOPROPYL-, 1-AMINO-2-BUTANOL, N,N-
BIS(2-AMINOETHYL)ETHANE-1,2-DIAMINE, N,N,2,2-TETRAMETHYL-1,3-
PROPANEDIAMINE, N,N-DIETHYL-1,3-PROPANEDIAMINE, N1-(2-AMINOETHYL)-N1-
METHYLETHANE-1,2-DIAMINE, N,N-DIMETHYL-1,3-PROPANEDIAMINE, 3,4,5-
TRIMETHOXYBENZYLAMINE, DL-1-(1-NAPHTHYL)ETHYLAMINE, (S)-(–)-1-(4-
METHYLPHENYL)ETHYLAMINE, (S)-(–)-BETA-METHYLPHENETHYLAMINE, (R)-(–)-
1-AMINOINDAN, (S)-(–)-1-PHENYLETHYLAMINE, (R)-(+)-1-PHENYLETHYLAMINE, 1-
PHENYLBUTAN-3-AMINE, D-PHENYLALANINOL, (1R,2S)-1-AMINO-2-INDANOL, 2-
AMINO-3,3-DIMETHYLBUTANE, 1,3-DIMETHYLBUTYLAMINE, 4-
(DIFLUOROMETHOXY)BENZYLAMINE, 2-N-PROPOXYETHYLAMINE, 2-
METHOXYETHYLAMINE, N-TERT-BUTOXYCARBONYL-3-AMINOPROPANAMINE, 3-
ISOPROPOXYPROPYLAMINE, 3-(METHYLTHIO)PROPYLAMINE, 2-AMINOETHYL
ISOPROPYL ETHER, 4-BROMO-2-FLUOROBENZYLAMINE, 4-IODOBENZYLAMINE, 4-
BROMOBENZYLAMINE, 2-(4-NITRO-PHENYL)-ETHYLAMINE, 3-FLUORO-5-

TABLE 5-continued

Synthon table (TRIFLUOROMETHYL)BENZYLAMINE, SEC-BUTYLAMINE, ISOPROPYLAMINE, 2-AMINO-1-METHOXYBUTANE, (S)-2-AMINO-1-PHENYLETHANOL, (S)-(+)-2-AMINO-1-PENTANOL, (R)-(−)-2-AMINO-1-BUTANOL, L-LEUCINAMIDE, CYCLOPENTYLAMINE, CYCLOPROPYLAMINE, TRANS-4-AMINOCYCLOHEXANOL, (1S,2S)-(+)-2-BENZYLOXYCYCLOHEXYLAMINE, (1R,2R)-(−)-2-BENZYLOXYCYCLOPENTYLAMINE, 4-NITRO-BENZYLAMINE, 3-BROMOBENZYLAMINE, 3-CHLORO-2,6-DIFLUOROBENZYLAMINE, 3,4-DICHLOROBENZYLAMINE, 4-(TRIFLUOROMETHYL)BENZYLAMINE, 2-(3-CHLOROPHENYL)ETHYLAMINE, 2-(4-CHLOROPHENYL)ETHYLAMINE, 3-CHLOROBENZYLAMINE, 2-CHLOROBENZYLAMINE, 3-FLUOROPHENETHYLAMINE, 4-FLUOROPHENETHYLAMINE, 3-FLUOROBENZYLAMINE, 2-(2-CHLOROPHENYL)ETHYLAMINE, 2-FLUOROPHENETHYLAMINE, (1R,2R)-(−)-2-AMINO-1-(4-NITROPHENYL)-1,3-PROPANEDIOL, 4-AMINOTETRAHYDROPYRAN, DL-HOMOCYSTEINE THIOLACTONE, DL-α-AMINO-EPSILON-CAPROLACTAM, INDAN-5-YLAMINE, 4-AMINOPYRIDINE, 2-(AMINOMETHYL)PIPERIDINE, 1-(3-AMINOPROPYL)-2-PIPECOLINE, BENZENEPROPANOIC ACID, β-(AMINOMETHYL)-, BENZENEACETIC ACID, α-(AMINOMETHYL)-, TETRAHYDROFURFURYLAMINE, 4-(2-AMINOETHYL)-1-BENZYLPIPERIDINE, (2,2-DIMETHYL-[1,3]-DIOXOLAN-4-YL)-METHYLAMINE, N-(3-AMINOPROPYL)MORPHOLINE, 4-(2-AMINOETHYL)MORPHOLINE, 2-(2-AMINOETHYL)-1-METHYLPYRROLIDINE, 4-(AMINOMETHYL)PIPERIDINE, 2-(AMINOMETHYL)-1-ETHYLPYRROLIDINE, 4-PYRROLIDINOBUTYLAMINE, 1-(3-AMINOPROPYL)PYRROLIDINE, 1-(3-AMINOPROPYL)-4-METHYLPIPERAZINE, N-(3'-AMINOPROPYL)-2-PYRROLIDINONE, BENZOIC ACID, 2-(AMINOMETHYL)-, 6-AMINOCAPROIC ACID, PENTANOIC ACID, 5-AMINO-, CYCLOHEXANECARBOXYLIC ACID, 4-(AMINOMETHYL)-, (2S)-4-AMINO-2-HYDROXY-BUTYRIC ACID, TYRAMINE, PHENOL, 2-(AMINOMETHYL)-, PHENOL, 4-(AMINOMETHYL)-, 3-METHOXYTYRAMINE, 2-FLUOROETHANAMINE, 3-AMINOPYRROLIDINE, 4-AMINOPIPERIDINE, ETHYL 4-AMINO-1-PIPERIDINECARBOXYLATE, ETHANONE, 2-AMINO-1-(4-MORPHOLINYL)-, 3-AMINOPROPANE-1,2-DIOL, 3-AMINOPROPIONITRILE, 3-AMINO-1-PROPANOL, 2-(2-AMINOETHOXY)ETHANOL, 2-(1H-INDOL-3-YL)ETHANAMINE (TRYPTAMINE), 3-(2-AMINOETHYL)PYRIDINE, 1H-INDOLE-2-METHANAMINE, ACETAMIDE, 2-AMINO-N-(1-METHYLETHYL)-, 2-(2-METHOXYPHENYL)ETHYLAMINE, 2-(AMINOMETHYL)PYRIDINE, PHENYLALANINE, 3,5-DIMETHYL-, GLUTAMIC ACID, BUTANOIC ACID, 2-AMINO-, D-PHENYLALANINE, 3-FLUORO-, BENZENEACETIC ACID, α-AMINO-4-FLUORO-, TYROSINE, 3-FLUORO-, 4-PYRIDINEPROPANOIC ACID, A-AMINO-, (αR)-, ASPARAGINE, BETA ALANINE NAPTHYLAMIDE, L-LEUCINE-4-NITROANILIDE, 2-AMINO-3-METHYL-3-SULFANYLBUTANOIC ACID, 1,2,3,4-TETRAHYDRO-1-NAPHTHYLAMINE, 4-(2-AMINOETHYL)PYRIDINE, 2-THIOPHENEMETHYLAMINE, 4-(AMINOMETHYL)PYRIDINE, 3-(AMINOMETHYL)PYRIDINE, 3-BROMO-4-METHOXYPHENETHYLAMINE, 3-FURANMETHANAMINE, 2-QUINOLINEMETHANAMINE, HOMOPIPERAZINE, PROPANAMIDE, 3-AMINO-N-METHYL-, 2-(2-FURYLMETHYLTHIO)ETHANAMINE, 4-(2-AMINOETHYL)BENZENESULFONAMIDE, 5-AMINOMETHYL-2-CHLOROPYRIDINE, (S)-(−)-1-(3-METHOXYPHENYL)ETHYLAMINE, (S)-(−)-1-(4-METHOXYPHENYL)ETHYLAMINE, CIS-2, 6 DIMETHYLPIPERAZINE, 3-PYRROLIDINECARBOXYLIC ACID, 3-PIPERIDINECARBOXYLIC ACID, 1H-IMIDAZOLE, 1-(3-PYRROLIDINYL)-, 5H-PYRROLO[3,4-B]PYRIDINE, 6,7-DIHYDRO-, PYRIDINE, 2-(3-PYRROLIDINYL)-, PYRROLIDINE, 3-(METHYLSULFONYL)-, 3-PYRROLIDINECARBOXAMIDE, PHENYLALANINE, 4-ETHYL-, 5-METHOXYTRYPTAMINE, N-ACETYLETHYLENEDIAMINE, S-(2-AMINOETHYL)ISOTHIOURONIUM BROMIDE, HOMOTAURINE, (R)-1-(3-METHOXYPHENYL)ETHYLAMINE, 2-(3,4-DIMETHOXYPHENYL)ETHYLAMINE, 3-METHOXYPHENETHYLAMINE, 2-(4-METHOXYPHENYL)ETHYLAMINE, 4-METHOXYBENZYLAMINE, 2-PHENOXYETHYLAMINE, 2-METHOXYBENZYLAMINE, 3-METHOXYBENZYLAMINE, PHENYLALANINE, 4-ETHYL-, BENZENEACETIC ACID, α-AMINO-, GLUTAMINE, BENZENEACETIC ACID, A-AMINO-4-HYDROXY-, (αR)-, BUTANOIC ACID, 2-AMINO-3-HYDROXY-, 3-THIOPHENEACETIC ACID, A-AMINO-, BENZOIC ACID, 2-AMINO-5-HYDROXY-, 4-AMINO-1-BUTANOL, 4-DIMETHYLAMINOBENZYLAMINE

What is claimed is:

1. A compound comprising the structure

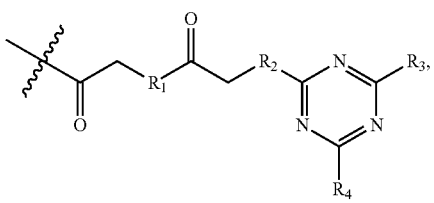

wherein the wavy line indicates the point of attachment to a substrate, optionally through a linker;

wherein $R_1$ is selected from the group consisting of 2-phenylpropylamine, 4-methylbenzylamine, 2-phenylethanamine, benzylamine, 3-phenylpropylamine, 2-methylbutylamine, isoamylamine, isobutylamine, butylamine, propargylamine, ethylamine, 1-amino-3,3-diethoxypropane, 4-amino-2-methyl-1-butanol, 5-amino-1-pentanol, acetamide, 4-(difluoromethoxy) benzylamine, 2-N-propoxyethylamine, 2-methoxyethylamine, 3-isopropoxypropylamine, 3-(methylthio) propylamine, 2-aminoethyl isopropyl ether, 4-bromo-2-fluorobenzylamine, 4-iodobenzylamine, 4-bromobenzylamine, 3-fluoro-5-(trifluoromethyl)benzylamine, 3-bromobenzylamine, 3-chloro-2,6-difluorobenzylamine, 3,4-dichlorobenzylamine, 4-(trifluoromethyl)benzylamine, 2-(3-chlorophenyl)ethylamine, 2-(4-chlorophenyl)ethylamine, 3-chlorobenzylamine, 2-chlorobenzylamine, 3-fluorophenethylamine, 4-fluorophenethylamine, 3-fluorobenzylamine, tetrahydrofurfurylamine, (2,2-dimethyl-[1,3]-dioxolan-4-yl)-methylamine, 3-amino-1-propanol, 2-(2-aminoethoxy)ethanol, 2-thiophenemethylamine, 3-bromo-4-methoxyphenethylamine, 3-furanmethanamine, propanamide, homotaurine, (r)-1-(3-methoxyphenyl)ethylamine, 2-(3,4-dimethoxyphenyl)ethylamine, 3-methoxyphenethylamine, 2-(4-methoxyphenyl)ethylamine, 4-methoxybenzylamine, 2-phenoxyethylamine, 2-methoxybenzylamine, and 3-methoxybenzylamine;

$R_2$ is selected from the group consisting of 2-phenylpropylamine, 4-methylbenzylamine, 2-phenylethanamine, benzylamine, 3-phenylpropylamine, 2-methylbutylamine, isoamylamine, isobutylamine, butylamine, propargylamine, ethylamine, 1-amino-3,3-diethoxypropane, 4-amino-2-methyl-1-butanol, 5-amino-1-pentanol, acetamide, 1-amino-2-butanol, 4-(difluoromethoxy)benzylamine, 2-N-propoxyethylamine, 2-methoxyethylamine, 3-isopropoxypropylamine, 3-(methylthio)propylamine, 2-aminoethyl isopropyl ether, 4-bromo-2-fluorobenzylamine, 4-iodobenzylamine, 4-bromobenzylamine, 3-fluoro-5-(trifluoromethyl)benzylamine, 3-bromobenzylamine, 3-chloro-2,6-difluorobenzylamine, 3,4-dichlorobenzylamine, 4-(trifluoromethyl)benzylamine, 2-(3-chlorophenyl)ethylamine, 2-(4-chlorophenyl)ethylamine, 3-chlorobenzylamine, 2-chlorobenzylamine, 3-fluorophenethylamine, 4-fluorophenethylamine, 3-fluorobenzylamine, tetrahydrofurfurylamine, (2,2-dimethyl-[1,3]-dioxolan-4-yl)-methylamine, 3-aminopropane-1,2-diol, 3-amino-1-propanol, 2-(2-aminoethoxy)ethanol, 2-(2-methoxyphenyl)ethylamine, 2-thiophenemethylamine, 3-bromo-4-methoxyphenethylamine, 3-furanmethanamine, propanamide, 2-(2-furylmethylthio)ethanamine, homotaurine, (r)-1-(3-methoxyphenyl)ethylamine, 2-(3,4-dimethoxyphenyl)ethylamine, 3-methoxyphenethylamine, 2-(4-methoxyphenyl)ethylamine, 4-methoxybenzylamine, 2-phenoxyethylamine, 2-methoxybenzylamine, 3-methoxybenzylamine, (z)-4-chloro-2-buten-1-amine, 2-(1-cyclohexenyl)ethylamine, 3-methoxypropylamine, 3-ethoxypropylamine, 3-N-propoxypropylamine, 2-ethoxyethylamine, 3-iodobenzylamine, 3-(trifluoromethyl)benzylamine, 4-(4-fluorophenoxy)benzylamine, 3,4-methylenedioxybenzylamine, 2-aminoethyl hydrogen sulfate, aminomethanesulfonic acid, 3,4,5-trimethoxybenzylamine, dl-1-(1-naphthyl)ethylamine, (s)-(−)-1-(4-methylphenyl)ethylamine, (s)-(−)-beta-methylphenethylamine, (r)-(−)-1-aminoindan, (s)-(−)-1-phenylethylamine, (r)-(+)-1-phenylethylamine, 1-phenylbutan-3-amine, d-phenylaninol, (1r,2s)-1-amino-2-indanol, 2-amino-3,3-dimethylbutane, 1,3-dimethylbutylamine, sec-butylamine, isopropylamine, 2-amino-1-methoxybutane, (s)-2-amino-1-phenylethanol, (s)-(+)-2-amino-1-pentanol, (r)-(−)-2-amino-1-butanol, cyclopentylamine, cyclopropylamine, trans-4-aminocyclohexanol, (1s,2s)-(+)-2-benzyloxycyclohexylamine, (1r,2r)-(−)-2-benzyloxycyclopentylamine, 2-(2-chlorophenyl)ethylamine, 2-fluorophenethylamine, 4-aminotetrahydropyran, dl-homocysteine thiolactone, indan-5-ylamine, 2-fluoroethanamine, (1r,2r)-(−)-2-amino-1-phenyl-1,3-propanediol, 2-amino-3-methyl-3-sulfanylbutanoic acid, (s)-(−)-1-(3-methoxyphenyl)ethylamine, (s)-(−)-1-(4-methoxyphenyl)ethylamine, 9-aminofluorene, 2,4,6-trimethylaniline, 2,4-dimethylaniline, 3,5-dimethyl aniline, 2,5-dimethylaniline, 2-methylaniline, 2,6-diethylaniline, 3-isopropylaniline, 4-isopropylaniline, 2,6-difluoroaniline, 3',4'-difluoroaniline, 3-chloroaniline, 2-chloroaniline, 2-fluoroaniline, 4-fluoroaniline, 3,4-methylenedioxy-1-aminobenzene, 4-ethoxyaniline, 2-(methylmercapto)aniline, 2-ethoxyaniline, o-anisidine, and 4-amino-1-butanol;

$R_3$ is selected from the group consisting of 2-phenylpropylamine, 4-methylbenzylamine, 2-phenylethanamine, benzylamine, 3-phenylpropylamine, 2-methylbutylamine, isoamylamine, isobutylamine, butylamine, propargylamine, ethylamine, 4-amino-2-methyl-1-butanol, 5-amino-1-pentanol, acetamide, 1-amino-2-butanol, 4-(difluoromethoxy)benzylamine, 3-(methylthio)propylamine, 4-bromo-2-fluorobenzylamine, 4-bromobenzylamine, 3-fluoro-5-(trifluoromethyl)benzylamine, 3-bromobenzylamine, 3-chloro-2,6-difluorobenzylamine, 3,4-dichlorobenzylamine, 4-(trifluoromethyl)benzylamine, 2-(3-chlorophenyl)ethylamine, 3-chlorobenzylamine, 2-chlorobenzylamine, 3-fluorophenethylamine, 4-fluorophenethylamine, tetrahydrofurfurylamine, (2,2-dimethyl-[1,3]-dioxolan-4-yl)-methylamine, 3-aminopropane-1,2-diol, 3-amino-1-propanol, 2-(2-aminoethoxy)ethanol, 2-(2-methoxyphenyl)ethylamine, 3-bromo-4-methoxyphenethylamine, 3-furanmethanamine, propanamide, 2-(2-furylmethylthio)ethanamine, (r)-1-(3-methoxyphenyl)ethylamine, 2-(3,4-dimethoxyphenyl)ethylamine, 2-(4-methoxyphenyl)ethylamine, 4-methoxybenzylamine, 2-phenoxyethylamine, 2-methoxybenzylamine, 3-methoxybenzylamine, (z)-4-chloro-2-buten-1-amine, 2-(1-cyclohexenyl)ethylamine, 3-methoxypropylamine, 3-ethoxypropylamine, 3-N-propoxypropylamine, 2-ethoxyethylamine, 3-iodobenzylamine, 3-(trifluoromethyl)benzylamine, 4-(4-fluorophenoxy)benzylamine, 3,4-methylenedioxybenzylamine, 2-aminoethyl hydrogen sulfate, aminomethanesulfonic acid, 3,4,5-trimethoxybenzylamine, dl-1-(1-naphthyl)ethylamine, (s)-(−)-1-(4-methylphenyl)ethylamine, 1-phenylbutan-3-amine, d-phenylalaninol, (1r,2s)-1-amino-2-indanol, 2-amino-3,3-dimethylbutane, 1,3-dimethylbutylamine, 2-amino-1-methoxybutane, (s)-2-amino-1-phenylethanol, (s)-(+)-2-amino-1-pentanol, cyclopentylamine, cyclopropylamine, trans-4-aminocyclohexanol, (1s,2s)-(+)-2-benzyloxycyclohexylamine, (1r,2r)-(−)-2-benzyloxycyclopentylamine, 2-(2-chlorophenyl)ethylamine, 2-fluorophenethylamine, 4-aminotetrahydropyran, dl-homocysteine thiolactone, indan-5-ylamine, benzenepropanoic acid, α-(aminomethyl)-benzoic acid, 6-aminocaproic acid, (2s)-4-amino-2-hydroxy-butyric acid, tyramine, 3-(aminomethyl)-, 3-methoxytyramine, 2-fluoroethanamine, phenylalanine, glutamic acid, tyrosine, 4-pyridinepropanoic acid, (1r,2r)-(−)-2-amino-1-phenyl-1,3-propanediol, beta alanine naphthylamide, 2-amino-3-methyl-3-sulfanylbutanoic acid, 1,2,3,4-tetrahydro-1-naphthylamine, (s)-(−)-1-(3-methoxyphenyl)ethylamine, (s)-(−)-1-(4-methoxyphenyl)ethylamine, 3-pyrrolidinecarboxylic acid, pyrrolidine, 9-aminofluorene, 2,6-diethylaniline, 3,4-methylenedioxy-1-aminobenzene, 4-ethoxyaniline, 1h-indol-5-ol, d-phenylalanine, 2-morpholineacetic acid, and 4-amino-1-butanol; and $R_4$ is selected from the group consisting of 2-phenylpropylamine, 4-methylbenzylamine, 2-phenylethanamine, benzylamine, 3-phenylpropylamine, 2-methylbutylamine, isoamylamine, isobutylamine, butylamine, propargylamine, (z)-4-chloro-2-buten-1-amine, 2-(1-cyclohexenyl)ethylamine, 3-methoxypropylamine, 3-ethoxypropylamine, 3-N-propoxypropylamine, 2-ethoxyethylamine, 3-iodobenzylamine, 3-(trifluoromethyl)benzylamine, 4-(4-fluorophenoxy)benzylamine, 3,4-methylenedioxybenzylamine, ethylamine, 1-amino-3,3-diethoxypropane, 4-amino-2-methyl-1-butanol, 5-amino-1-pentanol, acetamide, 1-amino-2-butanol, 3,4,5-trimethoxybenzylamine, dl-1-(1-naphthyl)ethylamine, (s)-(−)-1-(4-methylphenyl)ethylamine, (s)-(−)-beta-methylphenethylamine, (r)-(−)-1-aminoindan, (s)-(−)-1-phenylethylamine, (r)-(+)-1-phenylethylamine, 1-phenylbutan-3-amine, d-phenylalaninol, (1r,2s)-1-amino-2-indanol, 2-amino-3,3-dimethylbutane, 1,3-dimethylbutylamine, 4-(difluoromethoxy)benzylamine, 2-N-propoxyethylamine, 2-methoxyethylamine, 3-isopropoxypropylamine, 3-(methylthio)propylamine, 2-aminoethyl isopropyl ether, 4-bromo-2-fluorobenzylamine, 4-iodobenzylamine, 4-bromobenzylamine, 3-fluoro-5-(trifluoromethyl)benzylamine, sec-butylamine, isopropylamine, 2-amino-1-methoxybutane, (s)-2-amino-1-phenylethanol, (s)-(+)-2-amino-1-pentanol, (r)-(−)-2-amino-1-butanol, cyclopentylamine, cyclopropylamine, trans-4-aminocyclohexanol, (1s,2s)-(+)-2-benzyloxycyclohexylamine, (1r,2r)-(−)-2-benzyloxycyclopentylamine, 3-bromobenzylamine, 3-chloro-2,6-difluorobenzylamine, 3,4-dichlorobenzylamine, 4-(trifluoromethyl)benzylamine, 2-(3-chlorophenyl)ethylamine, 2-(4-chlorophenyl)ethylamine, 3-chlorobenzylamine, 2-chlorobenzylamine, 3-fluorophenethylamine, 4-fluorophenethylamine, 3-fluorobenzylamine, 2-(2-chlorophenyl)ethylamine, 2-fluorophenethylamine, 4-aminotetrahydropyran, dl-homocysteine thiolactone, indan-5-ylamine, tetrahydrofurfurylamine, (2,2-dimethyl-[1,3]-dioxolan-4-yl)methylamine, 6-aminocaproic acid, (2s)-4-amino-2-hydroxy-butyric acid, tyramine, 3-methoxytyramine, 2-fluoroethanamine, 3-aminopropane-1,2-diol, 3-amino-1-propanol, 2-(2-aminoethoxy)ethanol, 2-(1h-indol-3-yl)ethanamine (tryptamine), 2-(2-methoxyphenyl)ethylamine, phenylalanine, glutamic acid, tyrosine, 4-pyridinepropanoic acid, 2-amino-3-methyl-3-sulfanylbutanoic acid, 1,2,3,4-tetrahydro-1-naphthylamine, 2-thiophenemethylamine, 3-bromo-4-methoxyphenethylamine, 3-furanmethanamine, propanamide, 2-(2-furylmethylthio)ethanamine, (s)-(−)-1-(3-methoxyphenyl)ethylamine, (s)-(−)-1-(4-methoxyphenyl)ethylamine, 3-pyrrolidinecarboxylic acid, 3-piperidinecarboxylic acid, pyridine, pyrrolidine, 3-pyrrolidinecarboxamide, homotaurine, (r)-1-(3-methoxyphenyl)ethylamine, 2-(3,4-dimethoxyphenyl)ethylamine, 3-methoxyphenethylamine, 2-(4-methoxyphenyl)ethylamine, 4-methoxybenzylamine, 2-phenoxyethylamine, 2-methoxybenzylamine, 3-methoxybenzylamine, and 4-amino-1-butanol, and wherein the attachment point between the $R_1$-$R_4$ groups and the structure is through the N of the $R_1$-$R_4$ groups.

2. The compound of claim 1, wherein $R_1$ is 2-(2-aminoethoxy)ethanol, $R_2$ is 3-chloroaniline, $R_3$ is 9-aminofluorene, and $R_4$ is 2-amino-3-hydroxy-butanoic acid, and wherein the compound binds Rubisco at a pH between about 7 and about 11 and releases Rubisco or binds Rubisco with lower affinity at a pH between about 3 and about 7.

3. The compound of claim 1, wherein $R_1$ is (R)-1-(3-methoxyphenyl)ethylamine, $R_2$ is trans-4-aminocyclohexanol, $R_3$ is butylamine, and $R_4$ is 2-methylbutylamine, and wherein the compound binds Rubisco at a pH between about 4 and about 8 and releases Rubisco or binds Rubisco with lower affinity at a pH between about 7 and about 11.

4. The compound of claim 1, wherein $R_1$ is 3-fluoro-5-(trifluoromethyl)benzylamine, $R_2$ is 2,4,6-trimethylaniline, $R_3$ is 3-fluoro-5-(trifluoromethyl)benzylamine, and $R_4$ is indan-5-ylamine, or and wherein the compound binds leghemoglobin at a pH between about 7 and about 11 and releases leghemoglobin or binds leghemoglobin with lower affinity at a pH between about 3 and about 7.

5. The compound of claim 1, wherein the compound is conjugated to a substrate, optionally through a linker.

6. The compound of claim 5, wherein the substrate comprises agarose, sepharose, polystyrene, styrene, iron oxide, magnetic, or paramagnetic beads.

7. The compound of claim 5, wherein the substrate comprises silica, carboxyl functional groups, aldehyde functional groups, or N-hydroxysuccinimide functional groups.

8. The compound of claim 5, wherein the substrate comprises a functional group able to conjugate primary amines and thiols.

9. The compound of claim 5, wherein the substrate is a component of a chromatography resin.

* * * * *